(12) United States Patent
Karanja et al.

(10) Patent No.: US 9,322,022 B2
(45) Date of Patent: Apr. 26, 2016

(54) INHIBITION OF DNA2 IN FANCONI ANEMIA

(71) Applicant: California Institute of Technology, Pasadena, CA (US)

(72) Inventors: Kenneth Karanja, Pasadena, CA (US); Martin E. Budd, Pasadena, CA (US); Judith L. Campbell, Sierra Madre, CA (US)

(73) Assignee: CALIFORNIA INSTITUTE OF TECHNOLOGY, Pasadena, CA (US)

( * ) Notice: Subject to any disclaimer, the term of this patent is extended or adjusted under 35 U.S.C. 154(b) by 0 days.

(21) Appl. No.: 14/520,318

(22) Filed: Oct. 21, 2014

(65) Prior Publication Data

US 2015/0111950 A1 Apr. 23, 2015

Related U.S. Application Data

(60) Provisional application No. 61/893,703, filed on Oct. 21, 2013.

(51) Int. Cl.
*A61K 48/00* (2006.01)
*C07H 21/02* (2006.01)
*C07H 21/04* (2006.01)
*C12N 15/113* (2010.01)

(52) U.S. Cl.
CPC ........ *C12N 15/1137* (2013.01); *C12N 2310/14* (2013.01); *C12N 2320/31* (2013.01); *C12Y 306/04012* (2013.01)

(58) Field of Classification Search
CPC .............................. A61K 48/00; C12N 15/113
See application file for complete search history.

(56) References Cited

PUBLICATIONS

Scherer et al. (Nat. Biotechnol., 2003, 21(12), pp. 1457-1465).*
Zhang et al. (Current Pharmaceutical Biotechnology 2004, vol. 5, p. 1-7).*
Adamo, Adele et al.; "Preventing Nonhomologous End Joining Suppresses DNA Repair Defects of Fanconi Anemia"; Molecular Cell; 39; Jul. 9, 2010; pp. 25-35.
Bae, Sung-Ho et al.; "RPA governs endonuclease switching during processing of Okazaki fragments in eukaryotes"; Nature; vol. 412; Jul. 26, 2001; pp. 456-461.
Balakrishnan, Lata et al.; "Acetylation of Dna2 Endonuclease/Helicase and Flap Endonuclease 1 by p300 Promotes DNA Stability by Creating Long Flap Intermediates"; Journal of Biological Chemistry; vol. 285; No. 7; Feb. 12, 2010; pp. 4398-4404.
Bennardo, Nicole et al.; "Alternative-NHEJ is a Mechanistically Distinct Pathway of Mammalian Chromosome Break Repair"; PLoS Genetics; Jun. 2008; vol. 4; Issue 6; e1000110; 10pp.
Berkner, Kathleen L. et al.; "Abundant Expression of Polyomavirus Middle T Antigen and Dihydrofolate Reductase in an Adenovirus Recombinant"; Journal of Virology; vol. 61; No. 4; Apr. 1987; pp. 1213-1220.
Bout, Abraham et al.; "Lung Gene Therapy: In Vivo Adenovirus-Mediated Gene Transfer to Rhesus Monkey Airway Epithelium"; Human Gene Therapy 5; 1994; pp. 3-10.
Bouwman, Peter et al.; "The effects of deregulated DNA damage signalling on cancer chemotherapy response and resistance"; Nature Reviews; Cancer; vol. 12; Sep. 2012; pp. 587-598.

Budd, Martin E. et al.; "Interplay of Mre11 Nuclease with Dna2 plus Sgs1 in Rad51-Dependent Recombinational Repair"; PLoS One; Jan. 2009; vol. 4; Issue 1; e4267; 10pp.
Caillaud, Catherine et al.; "Adenoviral Vector as a Gene Delivery System into Cultured Rat Neuronal and Glial Cells"; European Journal of Neuroscience; vol. 5; 1993; pp. 1287-1291.
Cejka, Petr et al.; "DNA end resection by Dna2-Sgs1-RPA and its stimulation by Top3-Rmi1 and Mre11-Rad50-Xrs2"; Nature; Letters; vol. 467; Sep. 2, 2010; pp. 112-117.
Chan, Kok Lung et al.; "Replication stress induces sister-chromatid bridging at fragile site loci in mitosis"; Nature Cell Biology; vol. 11; No. 6; Jun. 2009; pp. 753-760 (23pp including sup. information).
Chen, Xuefeng et al.; "Cell cycle regulation of DNA double-strand break end resection by Cdk1-dependent Dna2 phosphorylation"; Nature Structural & Molecular Biology; Aug. 14, 2011; pp. 1-6.
Curtin, Nicola J.; "DNA repair dysregulation from cancer driver to therapeutic target"; Nature Reviews; Cancer; vol. 12; Dec. 2012; pp. 801-817.
Davidson, Dominique et al.; "Overproduction of Polyomavirus Middle T Antigen in Mammalian Cells through the Use of an Adenovirus Vector"; Journal of Virology; vol. 61; No. 4; Apr. 1987; pp. 1226-1239.
Davis, Mark E. et al.; "Evidence of RNAi in humans from systemically administered siRNA via targeted nanoparticles"; Nature; Letters; Apr. 15, 2010; vol. 464; pp. 1067-1071.
Dawson, Mark A. et al.; "Cancer Epigenetics: From Mechanism to Therapy"; Cell; vol. 150; Jul. 6, 2012; pp. 12-27.
Duxin, Julien P. et al.; "Human Dna2 is a Nuclear and Mitochondrial DNA Maintenance Protein"; Molecular and Cellular Biology; vol. 29; No. 15; pp. 4274-4282.
Duxin, Julien P. et al.; "Okazaki Fragment Processing-independent Role for Human Dna2 Enzyme during DNA Replication"; J. Biol. Chem; vol. 287; No. 26; Jun. 22, 2012; pp. 21980-21991.
Fattah, Farjana J. et al.; "Ku70, an essential gene, modulates the frequency of rAAV-mediated gene targeting in human somatic cells"; PNAS; vol. 105; No. 25; Jun. 24, 2008; pp. 8703-8708.
Gomez-Foix, Anna M. et al.; "Adenovirus-mediated Transfer of the Muscle Glycogen Phosphorylase Gene into Hepatocytes Confers Altered Regulation of Glycogen Metabolism"; The Journal of Biological Chemistry; vol. 267; No. 35; Dec. 15, 1992; pp. 25129-25134.
Gunn, Amanda et al.; "DNA and Chromosomes: Correct End Use during End Joining of Multiple Chromosomal Double Strand Breaks is Influenced by Repair Protein RAD50, DNA-dependent Protein Kinase DNA-PKcs, and Transcription Context"; The Journal of Biological Chemistry; vol. 286; No. 49; Dec. 9, 2011; pp. 42470-42482.
Guzman, Raul J. et al.; "Efficient Gene Transfer Into Myocardium by Direct Injection of Adenovirus Vectors"; Rapid Communication; Circulation Research; vol. 73; No. 6; Dec. 1993; pp. 1201-1207.

(Continued)

*Primary Examiner* — Amy Bowman
(74) *Attorney, Agent, or Firm* — Lewis Roca Rothgerber Christie LLP

(57) ABSTRACT

Inhibition of DNA2 in Fanconi anemia (FA) cells remedies the over-resection of DNA, thereby stabilizing the FA cells. Inhibition of DNA2 in FA cells allows for safe treatment of cancers in FA patients, a decrease in the lethality of FA cells, a decrease in bone marrow failure of FA patients, and a means for decreasing the incidence of cancer for FA patients.

7 Claims, 14 Drawing Sheets
(5 of 14 Drawing Sheet(s) Filed in Color)

(56) References Cited

PUBLICATIONS

Haj-Ahmad, Yousef et al.; "Development of a Helper-Independent Human Adenovirus Vector and Its Use in the Transfer of the Herpes Simplex Virus Thymidine Kinase Gene"; Journal of Virology; vol. 57; No. 1; Jan. 1986; pp. 267-274.

Heck, Henry d'A. et al.; "The implausibility of leukemia induction by formaldehyde: a critical review of the biological evidence on distant-site toxicity"; Regulatory Toxicology and Pharmacology 40; 2004; pp. 92-106.

Hwang, Do Won et al.; "A brain-targeted rabies virus glycoprotein-disulfide linked PEI nanocarrier for delivery of neurogenic microRNA"; Biomaterials; 32; 2011; pp. 4968-4975.

Itakura, Keiichi et al.; "Synthesis and Use of Synthetic Oligonucleotides"; Ann. Rev. Biochem.; 1984; 53; pp. 323-356.

Ansel, Howard C. et al.; "Peroral Solids, Capsules, Tablets, and Controlled-Release Dosage Forms"; Introduction to Pharmaceutical Dosage Forms; 4th Edition, 1985; pp. 126-138.

Karanja, Kenneth K. et al.; "DNA2 and EXO1 in replication-coupled, homology-directed repair and in the interplay between HDR and the FA/BRCA network"; Cell Cycle; vol. 11; No. 21; Nov. 1, 2012; pp. 3983-3996.

Karanja, Kenneth K. et al.; "Preventing over-resection by DNA2 helicase/nuclease suppresses repair defects in Fanconi anemia cells"; Cell Cycle; vol. 13; May 15, 2014; pp. 1-11.

Kirshenbaum, Lorrie A. et al.; "Highly Efficient Gene Transfer into Adult Ventricular Myocytes by Recombinant Adenovirus"; J. Clin. Invest.; vol. 92; Jul. 1993; pp. 381-387.

Kottemann, Molly C. et al.; "Fanconi anaemia and the repair of Watson and Crick DNA crosslinks"; Nature; vol. 493; Jan. 17, 2013; pp. 356-363.

Kumar, Priti et al.; "Transvascular delivery of small interfering RNA to the central nervous system"; Nature; vol. 448; Jul. 5, 2007; pp. 39-43.

La Salle, G. Le Gal et al.; "An Adenovirus Vector for Gene Transfer into Neurons and Glia in the Brain"; Science; vol. 259; Feb. 12, 1993; pp. 988-990.

Lin, Weiqiang et al.; "Mammalian DNA2 helicase/nuclease cleaves G-quadruplex DNA and is required for telomere integrity"; The EMBO Journal; 32; 2013; pp. 1425-1439.

Massie, Bernard et al.; "Construction of a Helper-Free Recombinant Adenovirus That Expresses Polyomavirus Large T Antigen"; Molecular and Cellular Biology; vol. 6; No. 8; Aug. 1986; pp. 2872-2883.

Morsy, Manal A. et al.; "Efficient Adenoviral-mediated Ornithine Transcarbamylase Expression in Deficient Mouse and Human Hepatocytes"; Rapid Publication; J. Clin. Invest.; vol. 92; Sep. 1993; pp. 1580-1586.

Moullier, Philippe et al.; "Correction of lysosomal storage in the liver and spleen of MPS VII mice by implantation of genetically modified skin fibroblasts"; Nature Genetics; vol. 4; Jun. 1993; pp. 154-159.

Nakanishi, Koji et al.; "Homology-directed Fanconi anemia pathway cross-link repair is dependent on DNA replication"; Nature Structural & Molecular Biology; vol. 18; No. 4; Apr. 2011; pp. 500-503.

Nakanishi, Koji et al.; "Homologous Recombination Assay for Interstrand Cross-Link Repair"; DNA Recombination; Methods in Molecular Biology; Chapter 16; 2011, vol. 745; pp. 283-291.

Narang, S. A. et al.; "Chemical Synthesis of Deoxyoligonucleotides by the Modified Triester Method"; Methods Enzymol.; vol. 65; 1980; pp. 610-620.

Nielsen, Peter E. et al.; "Peptide Nucleic Acid (PNA). A DNA Mimic with a Peptide Backbone"; Bioconjugate Chem.; 1994; 5; pp. 3-7.

Nimonkar, Amitabh V. et al.; "BLM-DNA2-RPA-MRN and EXO1-BLM-RPA-MRN constitute two DNA end resection machineries for human DNA break repair"; Genes & Development; vol. 25; 2011; pp. 350-362.

Pace, Paul et al.; "Ku70 Corrupts DNA Repair in the Absence of the Fanconi Anemia Pathway"; Science; vol. 329; Jul. 9, 2010; pp. 219-223.

Pulford, Bruce et al.; "Liposome-siRNA-Peptide Complexes Cross the Blood-Brain Barrier and Significantly Decrease $PrP^C$ on Neuronal Cells and $PrP^{RES}$ in Infected Cell Cultures"; PLoS One; vol. 5; Issue 6; Jun. 2010; e11085; 13pp.

Ragot, T. et al.; "Replication-defective recombinant adenovirus expressing the Epstein-Barr virus (EBV) envelope glycoprotein gp340/220 induces protective immunity against EBV-induced lymphomas in the cottontop tamarin"; Journal of General Virology; 1993; 74; pp. 501-507.

Rich, Devra P. et al.; "Development and Analysis of Recombinant Adenoviruses for Gene Therapy for Cystic Fibrosis"; Human Gene Therapy 4; 1993; pp. 461-476.

Redpath, John R. et al.; "Cells Deficient in the FANC/BRCA Pathway Are Hypersensitive to Plasma Levels of Formaldehyde"; Cancer Res; 67; (23); Dec. 1, 2007; pp. 11117-11122.

Roessler, Blake J. et al.; "Adenoviral-mediated Gene Transfer to Rabbit Synovium In Vivo"; J. Clin. Invest.; vol. 92; Aug. 1993; pp. 1085-1092.

Rohn, Susanne et al.; "RVG peptide as transfection reagent for specific cdk4 gene silencing in vitro and in vivo"; Journal of Drug Targeting; 2012; 20(4); pp. 381-388.

Roques, Celine et al.; "MRE11—RAD50—NBS1 is a critical regulator of FANCD2 stability and function during DNA double-strand break repair"; The EMBO Journal; 2009; 28; pp. 2400-2413.

Rosado, Ivan V. et al.; "Formaldehyde catabolism is essential in cells deficient for the Fanconi anemia DNA-repair pathway"; Nature Structural & Molecular Biology; vol. 18; No. 12; Dec. 2011; pp. 1432-1434.

Russell, David W. et al.; "Human gene targeting by viral vectors"; Nature Genetics; vol. 18; Apr. 1998; pp. 325-330.

Trujillo, Juan P. et al.; On the role of FAN1 in Fanconi anemia; Blood; vol. 120; No. 1; Jul. 5, 2012; pp. 86-89.

Zabner, Joseph et al.; "Adenovirus-Mediated Gene Transfer Transiently Corrects the Chloride Transport Defect in Nasal Epithelia of Patients with Cystic Fibrosis"; Cell; vol. 75; Oct. 22, 1993; pp. 207-216.

Zabner, Joseph et al.; "Safety and efficacy of repetitive adenovirus-mediated transfer of CFTR cDNA to airway epithelia of primates and cotton rats"; Nature Genetics; vol. 6; Jan. 1994; pp. 75-83.

Zhang, W.-W. et al.; "Generation and Identification of Recombinant Adenovirus by Liposome-Mediated Transfection and PCR Analysis"; BioTechniques; vol. 15; No. 5; 1993; pp. 868-872.

Zuckerman, Jonathan E. et al.; "Correlating animal and human phase Ia/Ib clinical data with CALAA-01, a targeted, polymer-based nanoparticle containing siRNA"; PNAS; Aug. 5, 2014; vol. 111; No. 31; pp. 11449-11454.

Strauss, Carmit et al.; "The DNA2 nuclease/helicase is an estrogen-dependent gene mutated in breast and ovarian cancers"; Oncotarget; Sep. 6, 2014; 14pp.

Stark, Jeremy M. et al.; "Genetic Steps of Mammalian Homologous Repair with Distinct Mutagenic Consequences"; Molecular and Cellular Biology; Nov. 2004; vol. 24; No. 21; pp. 9305-9316.

Niu, Hengyao et al.; "Mechanism of the ATP-dependent DNA end-resection machinery from *Saccharomyces cerevisiae*"; Nature; vol. 467; Sep. 2, 2010; pp. 108-112.

\* cited by examiner

INHIBITION OF DNA2 IN FANCONI ANEMIA

CROSS-REFERENCE TO RELATED APPLICATION(S)

The present application claims priority to and the benefit of U.S. Provisional Application Ser. No. 61/893,703 filed on Oct. 21, 2013, the entire contents of which are incorporated herein by reference.

STATEMENT REGARDING FEDERALLY SPONSORED RESEARCH OR DEVELOPMENT

This invention was made with government support under GM100196 awarded by the National Institutes of Health. The government has certain rights in the invention.

SEQUENCE LISTING

The instant application contains a Sequence Listing which has been submitted in ASCII format via EFS-Web and is hereby incorporated by reference in its entirety. Said ASCII copy, created on Dec. 30, 2014, is named SEQLISTING75729.txt and is 628 bytes in size.

BACKGROUND

Fanconi anemia (FA) is a rare hereditary disease characterized by chromosomal instability, developmental abnormalities, bone marrow failure and a predisposition to cancer. The instability of FA patients' cells renders chemotherapeutic and radiation treatments often times lethal for the patient. Curiously, while FA is a relatively rare disease, the FA proteins participate in a common fundamental DNA replication/repair pathway—i.e. the FA/BRCA pathway.

FA may be classified into 16 complementation groups each associated with a defective FA gene. The FA gene products participate in the FA/breast cancer allele (FA/BRCA) DNA repair pathway, which is responsible for genome maintenance after DNA:DNA crosslinks, DNA:protein crosslinks, and S-phase replication stress. While the study of the repair of interstrand crosslinks has been instrumental in defining the players in the FA/BRCA network, the endogenous causes of DNA damage underlying the pathogenesis of Fanconi anemia are not fully identified. A more complete understanding of the interplay of the components in the FA/BRCA pathway is necessary to provide a non-lethal therapy for cancers in both FA cells and FA-like cells, as well as help remedy bone marrow failure in FA patients.

SUMMARY

Aspects of embodiments of the present invention are directed to methods of inhibiting DNA2 in Fanconi anemia cells and Fanconi-anemia-like cells to thereby alleviate the damage caused by DNA2 in FA cells and FA-like cells.

In some embodiments of the present invention, a method of treating a Fanconi anemia patient or a Fanconi anemia-like patient having a cancer for chemotherapy or radiation therapy, includes inhibiting DNA2 in cells of the Fanconi anemia patient or the Fanconi anemia-like patient.

In some embodiments of the present invention, a method of priming a Fanconi anemia patient or a Fanconi anemia-like patient having a cancer for chemotherapy or radiation therapy, includes inhibiting DNA2 in cells of the Fanconi anemia patient or the Fanconi anemia-like patient.

In some embodiments of the present invention, a method of decreasing lethality of Fanconi anemia cells or Fanconi-anemia-like cells includes inhibiting DNA2 in the Fanconi anemia cells or Fanconi anemia-like cells.

In some embodiments of the present invention, a method of decreasing bone marrow failure in Fanconi anemia patients includes inhibiting DNA2 in hematopoietic cells of the Fanconi anemia patients.

In some embodiments of the present invention, a method of decreasing the incidence of cancer in a Fanconi anemia patient or a Fanconi anemia-like patient includes inhibiting DNA2 in cells of the Fanconi anemia patient or Fanconi anemia-like patient.

In some embodiments of the present invention, the inhibition of DNA2 includes disrupting a DNA2 gene, disrupting a DNA2 allele, mutating a DNA2 gene, inhibiting transcription of a DNA2 gene, inhibiting translation of a DNA2 transcript, inhibiting post-translational modification of DNA2, inhibiting DNA2 protein activity, inhibiting modulators of DNA2 protein activity, or a combination thereof.

BRIEF DESCRIPTION OF THE DRAWINGS

The patent or application file contains at least one drawing executed in color. Copies of this patent or patent application publication with color drawings will be provided by the Office upon request and payment of the necessary fee.

These and other features and advantages of the present invention will be better understood by reference to the following detailed description when considered in conjunction with the accompanying drawings.

DETAILED DESCRIPTION

In addition to bone marrow failure, FA patients suffer from a predisposition to several cancers. Because of the genetic defect in DNA repair, cells from FA patients are often lethally sensitive to chemotherapeutic drugs and radiation that damage or interfere with DNA. For example, the FANCD2 protein is required for the repair of DNA damage by the FA/BRCA pathway, and consequently FANCD2-deficient cells are sensitive to compounds such as cisplatin and formaldehyde that induce DNA:DNA and DNA:protein crosslinks, respectively.

Moreover, mutations in the FA pathway, for example FAN1, may lead to some, but not enough of the symptoms to lead to a diagnosis or characterization of FA. These mutations result in "Fanconi anemia-like cells" and "Fanconi anemia-like patients." (Trujillo et al., 2012, *Blood*, 120:96-99 and Kotteman and Smorgorzewska, *Nature*, 493:356-363, the entire contents of both of which are herein incorporated by reference.) Accordingly, methods disclosed herein directed to FA cells and FA patients may also be directed to FA-like cells and FA-like patients having mutations in the FA/BRCA pathway.

Figure 1:
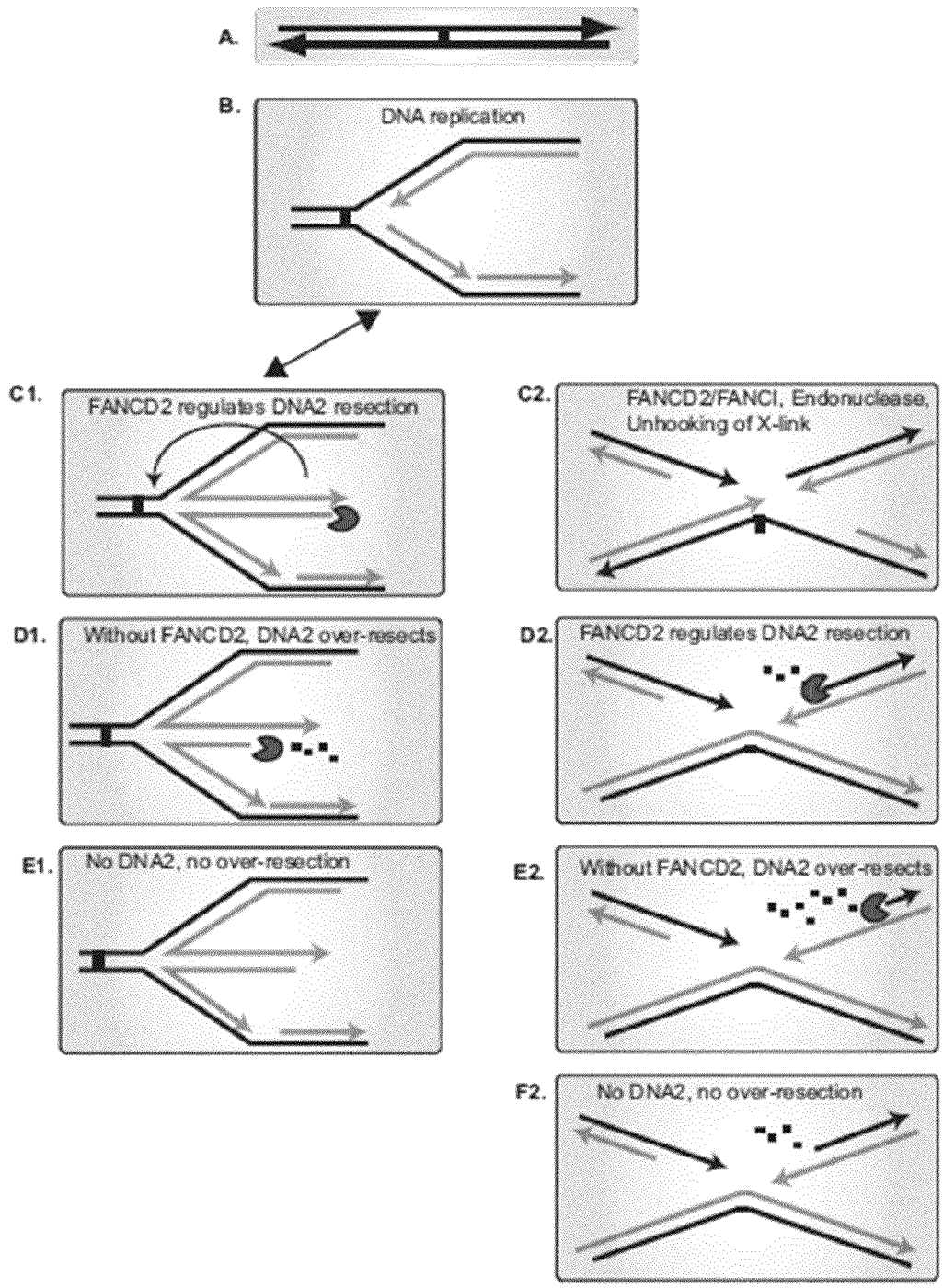
FIG. 1 is a schematic depicting the proposed roles in steps A, B, C1, D1, E1, C2, D2, E2, and F2 of DNA2 and FANCD2 during DNA repair and replication stress. Step A shows a replication fork that is stalled by an interstrand cross-link (ICL) or DNA-protein crosslink (DPC) or other impediment, as indicated by the black square. Step B shows replication is halted at the impediment and various proteins are recruited including FANCM/FAAP24 and the FA core complex. Step C1 represents Fork protection in which fork regression occurs to form a chicken foot structure, and FANCD2 is required to prevent resection of nascent DNA. Step D1 represents FANCD2$^{-/-}$ cells in which DNA2 excessively resects nascent DNA. Step E1 represents FANCD2$^{-/-}$ cells in which depletion of DNA2 inhibits excessive resection, thereby allowing the cells to survive. Step C2 represents FA/BRCA repair pathway in which during ICL repair, FANCD2/FANCI recruits nucleases to unhook the crosslink. Step D2 shows FANCD2 regulating resection using nucleases to generate 3' DNA ends suitable for homology directed repair (HDR). Step E2 represents FANCD2$^{-/-}$ cells in which DNA2 and other nucleases excessively resect the DNA at the double strand break (DSB). Step F2 represents FANCD2$^{-/-}$ cells in which depletion of DNA2 prevents excessive resection, thereby allowing the cells to survive.

As disclosed herein, aspects of embodiments of the present invention are directed to the regulation by FANCD2 of the DNA2 helicase/nuclease in the resection of double strand breaks (DSBs) during homology directed repair (HDR) of replication induced damage (FIG. 1). For example, in non-FA cells (e.g., wild type cells), FANCD2 modulates DNA2 to ensure that over-resection of DNA does not occur. As such, in FA cells, represented herein by FANCD2$^{-/-}$ cells, the regulation of the DNA2 enzyme is impaired, and the unregulated DNA2 over-resects during DNA repair, rendering insufficient and incomplete replication. This impaired replication in FA cells results in the chromosomal instability, developmental abnormalities, bone marrow failure and cancers found in FA patients.

In some embodiments of the present invention, inhibition of DNA2 in FA cells provides a remedy for the over-resection of DNA, thereby stabilizing the FA cells. In some embodiments, inhibition of DNA2 in FA cells or FA-like cells decreases the lethality of the FA cells or FA-like cells. That is, as inhibition of DNA2 stabilizes these cells, the cells have decreased over-resecting DNA and have increased proliferation compared to FA cells or FA-like cells without DNA2 inhibition.

In some embodiments of the present invention, inhibition of DNA2 decreases bone marrow failure in FA patients. FA cells have fewer hematopoietic stem cells and progenitor cells because they are not able to proliferate, resulting in bone marrow failure in FA patients. (Kottemann and Smogorzewska, 2013, *Nature*, 493, 356-363, the entire contents of which are herein incorporated by reference.) As stabilization of FA cells by inhibition of DNA2 increases cell proliferation, inhibition of DNA2 in FA cells, including hematopoietic stem cells and progenitor cells, results in a decrease in bone marrow failure.

Because an FA patient's cells are impaired with over-resecting DNA2, DNA-damaging chemotherapy and radiation is often lethal for FA patients. In an FA patient with cancer, inhibition of DNA2 in FA cells mimics a more chromosomally stable non-FA cell, thereby stabilizing the non-cancer FA cells and allowing for chemotherapy and/or radiation targeting of the cancer cells. In this way, inhibition of DNA2 in cells of an FA or FA-like patient having cancer prior to or in combination with chemotherapeutic agents or radiation, allows for the chemotherapy or radiation to target the cancer cells (i.e., priming the cells or priming the FA or FA-like patient for treatment) without being potentially lethal to all of the patient's cells. As used herein, the term "priming" refers to stabilizing the FA or FA-like cells in a FA or FA-like patient having cancer with inhibition of DNA2 in order to reduce the lethality or toxicity of the chemotherapy or radiation therapy to the patient. While the chemotherapy or radiation therapy may be administered to the patient after inhibition of DNA2 in the patient's cells, priming does not preclude simultaneous inhibition of DNA2 with either chemotherapy or radiation therapy.

In some embodiments, a method of treating an FA patient having a cancer or an FA-like patient having a cancer with chemotherapy or radiation therapy, includes inhibiting DNA2 in the cells of the FA patient or FA-like patient, prior to or in combination with the chemotherapy or radiation therapy.

The lethal sensitivity of FA cells to chemotherapy may be mechanistically explained by the overlap of the FA pathway and the DNA replication and repair pathways. For example, FA cells are at least sensitive to chemotherapy that damages DNA, inhibits DNA synthesis, and/or interferes with the DNA damage response.

The aberrant mechanisms in the Fanconi anemia (FA) pathway overlap with tumorigenesis, thereby predisposing FA patients to many types of cancer. The interplay of the FA and tumorigenic pathways is disclosed herein and summarized previously. (Curtin, 2012, *Nat. Reviews Cancer*, 12:801-817 and Bouwman and Jonkers, 2012, *Nat. Reviews Cancer*, 12:587-598, the entire contents of both of which are herein incorporated by reference.) In FA cells and FA-like cells, the unregulated and over-resecting DNA2 renders a high incidence of cancer, whereby inhibition of DNA2 in FA patients decreases the chances for the aberrant mechanism to lead to cancer. Accordingly, inhibition of DNA2 in cells of an FA patient or an FA-like patient decreases the incidence of cancer relative to an FA patient or FA-like patient without DNA2 inhibition.

As used herein, "DNA2" may refer to the DNA2 gene, a DNA2 allele, a DNA2 transcript, a DNA2 protein, including a DNA2 protein with post-translational modifications.

As used herein, "inhibiting DNA2," "inhibition of DNA2," and like terms refer to the inhibition of any form of DNA2 as that term is defined above.

As used herein, "inhibit," "inhibiting," "inhibition," and like terms refer to a decrease in an activity, response, condition, disease, or other biological parameter, as compared to native or control levels. This may include, but is not limited to, the complete loss of DNA2 activity, response, condition, or disease. This may also include, for example, a 10% reduction in the activity, response, condition, or disease as compared to the native or control level. Thus, the reduction may be a 10, 20, 30, 40, 50, 60, 70, 80, 90, 100%, or any amount of reduction in between as compared to native or control levels.

"Promote," "promotion," and "promoting" refers to an increase in an activity, response, condition, disease, or other biological parameter, as compared to native or control levels. This may include but is not limited to the initiation of the activity, response, condition, or disease. This may also include, for example, a 10% increase in the activity, response, condition, or disease as compared to the native or control level. Thus, the increase may be a 10, 20, 30, 40, 50, 60, 70, 80, 90, 100%, or any amount of increase in between as compared to native or control levels.

As used herein, "treat," "treating," "treatment," and like terms refer to a method of reducing the effects of a disease or condition compared to native or control levels. These terms may also refer to a method of reducing the underlying cause of the disease or condition itself rather than just the symptoms. Additionally, treatment of cancer in an FA patient or an FA-like patient includes stabilizing some or all of the cells of the FA patient or FA-like patient in combination with sensitizing the cancer cells for chemotherapy or radiation. The treatment may be any reduction from native levels and may be, but is not limited to, the complete ablation of the disease, condition, or the symptoms of the disease or condition. For example, a disclosed method for stabilizing FA cells may be considered to be a treatment if there is a 10% reduction in one or more symptoms of the disease in a subject with the disease when compared to native levels in the same subject or control subjects. For example, in some embodiments, the reduction may be a 10, 20, 30, 40, 50, 60, 70, 80, 90, 100%, or any amount of reduction in between as compared to native or control levels.

As used herein, "subject" includes, but is not limited to, animals, plants, bacteria, viruses, parasites and any other organism or entity that has nucleic acids. The subject may be a vertebrate, for example, a mammal (e.g., a human, horse, pig, rabbit, dog, sheep, goat, non-human primate, cow, cat, guinea pig or rodent), a fish, a bird, a reptile or an amphibian. The subject may also be an invertebrate, for example, an arthropod (e.g., insects and crustaceans). The term "subject" does not denote a particular age or sex. Thus, adult and newborn subjects, as well as fetuses, whether male or female, are included in the term "subject."

As used herein, "patient" refers to a subject afflicted with a disease or disorder—e.g., Fanconi anemia (FA). The term "patient" includes human and veterinary subjects.

Inhibition of DNA2

According to embodiments of the present invention, DNA2 may be inhibited using any suitable technique known in the art for inhibition. For inhibition of a DNA2 gene, methods may include complete or partial gene disruption, and/or mutation of the DNA2 gene locus. Inhibition of DNA2 may include any type of disruption of, or mutation to, any DNA2 allele. Inhibition of DNA2 may include inhibiting transcription of DNA2, inhibiting translation of a DNA2 transcript, inhibiting post-translational modification of DNA2, inhibiting DNA2 protein activity, inhibiting modulators of DNA2 protein activity, or any combination of these methods.

According to embodiments of the present invention, inhibition of DNA2 may occur in vitro or in vivo. Methodologies for inhibiting DNA2 in an in vitro cell culture are known in the art, examples of which are disclosed herein. In vitro DNA2 gene and allele disruption and shRNA inhibition of DNA2 are disclosed in the Examples herein. Methods disclosed herein for in vivo DNA2 inhibition may be readily applied in vitro, as would be understood by one having ordinary skill in the art.

Methods for inhibition of DNA2 in vivo (i.e., in a subject) are also known in the art. For example, RNAi (e.g., siRNA, shRNA, miRNA) may be packaged for delivery in subjects, including human patients, by a method known in the art. For example, RNAi in nanoparticles for human therapy has been previously described. (Davis et al., 2010, Nature, 464:1067-1071 and Zuckerman et al., 2014, PNAS, 31: 11449-11454, the entire contents of both of which are herein incorporated by reference.) Additional uses and applications of siRNA, hsRNA or microRNA are described in Kumar et al., Nature 448: 39-43, 2007; Pulford et al., PLoS One 5:e11085, 2010; Rohn et al., J. Drug Target, 20: 381-388, 2012, and Hwang do et al., Biomaterials, 32: 4968-4975, 2011, the entire contents of all of which are incorporated herein by reference.

In some embodiments, methods for inhibition of DNA2 by gene or allelic disruption may include viral vectors. Viral vectors provide molecules which are capable of integration into a mammalian chromosome without substantial toxicity. The construction of replication-defective adenoviruses has been described (Berkner et al., J. Virology 61:1213-1220 (1987); Massie et al., Mol. Cell. Biol. 6:2872-2883 (1986); Haj-Ahmad et al., J. Virology 57:267-274 (1986); Davidson et al., J. Virology 61:1226-1239 (1987); Zhang "Generation and identification of recombinant adenovirus by liposome-mediated transfection and PCR analysis" BioTechniques 15:868-872 (1993), the entire contents of all of which are herein incorporated by reference). One benefit of using these viruses as vectors is that they are limited in the extent to which they may spread to other cell types, since they replicate within an initial infected cell, but are unable to form new infectious viral particles.

Recombinant adenoviruses have been shown to achieve high efficiency gene transfer after direct, in vivo delivery to airway epithelium, hepatocytes, vascular endothelium, CNS parenchyma and a number of other tissue sites (Morsy, J. Clin. Invest. 92:1580-1586 (1993); Kirshenbaum, J. Clin. Invest. 92:381-387 (1993); Roessler, J. Clin. Invest. 92:1085-1092 (1993); Moullier, Nature Genetics 4:154-159 (1993); La Salle, Science 259:988-990 (1993); Gomez-Foix, J. Biol. Chem. 267:25129-25134 (1992); Rich, Human Gene Therapy 4:461-476 (1993); Zabner, Nature Genetics 6:75-83 (1994); Guzman, Circulation Research 73:1201-1207 (1993); Bout, Human Gene Therapy 5:3-10 (1994); Zabner, Cell 75:207-216 (1993); Caillaud, Eur. J. Neuroscience 5:1287-1291 (1993); and Ragot, J. Gen. Virology 74:501-507 (1993), the entire contents of all of which are herein incorporated by reference).

Another type of viral vector is based on an adeno-associated virus (AAV). This defective parvovirus may infect many cell types and is nonpathogenic to humans. AAV type vectors transport about 4 to 5 kb and wild type AAV is known to stably insert into chromosome 19.

In another type of AAV virus, the AAV contains a pair of inverted terminal repeats (ITRs) which flank at least one cassette containing a promoter which directs cell-specific expression operably linked to a heterologous gene. Heterologous in this context refers to any nucleotide sequence or gene which is not native to the AAV or B 19 parvovirus. The AAV and B 19 coding regions have been deleted, resulting in a safe, noncytotoxic vector. The AAV ITRs, or modifications thereof, confer infectivity and site-specific integration, but not cytotoxicity, and the promoter directs cell-specific expression. U.S. Pat. No. 6,261,834 is herein incorporated by reference in its entirety for material related to the AAV vector.

Other useful systems include, for example, replicating and host-restricted non-replicating vaccinia virus vectors.

DNA2 inhibition may be delivered to the target cells in a variety of ways. For example, methods of inhibiting DNA2 as disclosed herein may be delivered through electroporation, or through lipofection, or through calcium phosphate precipitation. The delivery mechanism chosen will depend in part on the type of cell targeted and whether the delivery is occurring for example in vivo or in vitro.

Nucleic acids that are delivered to cells which are to be integrated into the host cell genome, typically contain integration sequences. These sequences are often viral related sequences, particularly when viral based systems are used. These viral integration systems may also be incorporated into nucleic acids which are to be delivered using a non-nucleic acid based system of delivery, such as a liposome, so that the nucleic acid contained in the delivery system may become integrated into the host genome.

Other techniques for integration into the host genome include, for example, systems designed to promote homologous recombination with the host genome. These systems typically rely on sequences flanking the nucleic acid to be expressed, where the flanking sequence has enough homology with a target sequence within the host cell genome that recombination between the vector nucleic acid and the target nucleic acid takes place, causing the delivered nucleic acid to be integrated into the host genome. These systems and the methods necessary to promote homologous recombination are known to those skilled in the art.

Methods for inhibiting DNA2 may include delivery to the subject's cells in vivo and/or ex vivo by a variety of mechanisms well known in the art (e.g., uptake of naked DNA, liposome fusion, intramuscular injection of DNA via a gene gun, endocytosis and the like).

If ex vivo methods are employed, cells or tissues may be removed and maintained outside the body according to standard protocols well known in the art. The compositions may be introduced into the cells via any gene transfer mechanism, such as, for example, calcium phosphate mediated gene delivery, electroporation, microinjection or proteoliposomes. The transduced cells may then be infused (e.g., in a pharmaceutically acceptable carrier) or homotopically transplanted back into the subject per standard methods for the cell or tissue type. Standard methods are known for transplantation or infusion of various cells into a subject.

In some embodiments, a method of inhibiting DNA2 in an FA subject, comprising administering to the subject a composition for inhibiting DNA2 (e.g., nucleic acids (RNAi), proteins, antibodies, and vectors) in a pharmaceutically acceptable carrier.

Methods for inhibiting transcription of DNA2 may include any suitable method. For example, epigenetic inhibition of DNA2 includes inhibiting DNA2 transcription without disrupting the DNA2 coding sequence. Non-limiting examples of epigenetic inhibition of transcription of DNA2 include DNA methylation, chromatin modification, and long non-coding RNA (lncRNA). Methods of epigenetic inhibition are known in the art as described in, e.g., Dawson and Kouzarides, 2012, *Cell*, 150:12-27, the entire contents of which are herein incorporated by reference.

Methods for inhibiting post-translational modifications are known in the art. Non-limiting examples of post-translational modifications include acetylation and phosphorylation. For example, deacetylation of DNA2 is known to inhibit DNA2 as previously described (Balakrishnan et al., 2010, *JBC*, 285: 4398-4404, the entire contents of which are herein incorporated by reference). Additionally, DNA2 is phosphorylated and DNA2 activity is dependent on phosphorylation. Inhibition of phosphorylation of DNA2 inhibits DNA2 activity as previously described (Chen et al., 2011, 18:1015-1019, the entire contents of which are herein incorporated by reference.)

Methods for inhibiting DNA2 by inhibiting modulators of DNA2 include the proteins BLM and RPA. Inhibition of BLM results in a decrease of DNA2 activity as previously described, for example, in Cejka et al., 2010, *Nature*, 467: 112-117 and Nimonkar et al., 2011, *Genes & Development*, 25:350-362, the entire contents of both of which are herein incorporated by reference. Inhibition of RPA results in a decrease of DNA2 activity as previously described, for example, in Bae et al., 2001, *Nature*, 412:456-461 and Nimonkar et al., 2001, supra, the entire contents of both of which are herein incorporated by reference.

Methods for synthesizing nucleic acids, proteins, and vectors are well known in the art. For example, nucleic acids may be made using standard chemical synthesis methods or may be produced using enzymatic methods or any other known method. Such methods may range from standard enzymatic digestion followed by nucleotide fragment isolation (see for example, Sambrook et al., Molecular Cloning: A Laboratory Manual, 2nd Edition (Cold Spring Harbor Laboratory Press, Cold Spring Harbor, N.Y., 1989) Chapters 5, 6, the entire contents of which are herein incorporated by reference) to purely synthetic methods, for example, by the cyanoethyl phosphoramidite method using a Milligen or Beckman System 1Plus DNA synthesizer (for example, Model 8700 automated synthesizer of Milligen-Biosearch, Burlington, Mass. or ABI Model 380B). Synthetic methods useful for making oligonucleotides are also described by Ikuta et al., Ann. Rev. Biochem. 53:323-356 (1984), (phosphotriester and phosphite-triester methods), and Narang et al., Methods Enzymol., 65:610-620 (1980), (phosphotriester method), the entire contents of both of which are herein incorporated by reference. Protein nucleic acid molecules may be made using known methods such as those described by Nielsen et al., Bioconjug. Chem. 5:3-7 (1994), the entire contents of which are herein incorporated by reference.

The terms "composition," "pharmaceutical composition," and like terms are used interchangeably herein and refer to compositions or formulations that in addition to a composition for inhibiting DNA2, may also include an excipient, such as a pharmaceutically acceptable carrier that is conventional in the art and that is suitable for administration to mammals, and, for example, humans or human cells. Such compositions may be formulated for administration via one or more of a number of routes, including but not limited to, oral, parenteral, intravenous, intraarterial, subcutaneous, intranasal, sublingual, intraspinal, intracerebroventricular, and the like. Cells which may be part of or from a subject can be administered a composition as disclosed herein, for example, for therapeutic, diagnostic, or prophylactic purposes. The cells may also be cultured, for example, cells as part of an assay for screening potential pharmaceutical compositions, and the cells may be part of a transgenic animal for research purposes. In addition, compositions for topical (e.g., oral mucosa, respiratory mucosa) and/or oral administration may form solutions, suspensions, tablets, pills, capsules, sustained-release formulations, oral rinses, or powders, as known in the art are contemplated herein. The compositions also may include stabilizers and preservatives. For examples of carriers, stabilizers and adjuvants, see University of the Sciences in Philadelphia (2005) Remington: The Science and Practice of Pharmacy with Facts and Comparisons, 21st Ed, the entire contents of which are herein incorporated by reference.

Compositions including a DNA2 inhibitor as disclosed herein, may be administered by any convenient route, including parenteral, enteral, mucosal, topical, e.g., subcutaneous, intravenous, topical, intramuscular, intraperitoneal, transdermal, rectal, vaginal, intranasal or intraocular. In some embodiments, the compositions as disclosed herein are not topically administered. In some embodiments, the delivery may be by oral administration of the composition formulation. In one embodiment, the delivery may be by intranasal administration of the composition, especially for use in therapy of the brain and related organs (e.g., meninges and spinal cord). Along these lines, intraocular administration is also possible. In another embodiment, delivery may be achieved by intravenous (i.v.) administration of the composition, which is especially advantageous when a longer-lasting i.v. formulation is desired. Suitable formulations may be found in Remington's Pharmaceutical Sciences, 16th and 18th Eds., Mack Publishing, Easton, Pa. (1980 and 1990), and Introduction to Pharmaceutical Dosage Forms, 4th Edition, Lea & Febiger, Philadelphia (1985), each of which is incorporated herein by reference.

A composition that inhibits DNA2 by a method as disclosed herein may be administered in prophylactically or therapeutically effective amounts. The targeted delivery compositions may be administered along with a pharmaceutically acceptable carrier. A "prophylactically" or "therapeutically effective amount" means that amount necessary, at least partly, to attain the desired effect, or to delay the onset of inhibit the progression of, or halt altogether, the onset or progression of the particular disease or disorder being treated. Such amounts will depend, of course, on the particular condition being treated, the severity of the condition and individual patient parameters including age, physical condition, size, weight and concurrent treatment. These factors are well known to those of ordinary skill in the art and may be addressed with no more than routine experimentation. In some embodiments, a maximum dose may be used, that is, the highest safe dose according to sound medical judgment. It will be understood by those of ordinary skill in the art, however, that a lower dose or tolerable dose may be administered for medical reasons, psychological reasons or for virtually any other reasons.

As used herein, the term "pharmaceutically acceptable carrier" refers to a pharmaceutically acceptable material, composition or vehicle, such as a liquid or solid filler, diluent, excipient, solvent or encapsulating material, involved in carrying or transporting the composition that inhibits DNA2 from one organ, or portion of the body, to another organ, or portion of the body. Each carrier must be "acceptable" in the sense of being compatible with the other ingredients of the formulation and is compatible with administration to a subject, for example a human. For the clinical use of the methods of the present invention, targeted delivery compositions according to embodiments of the present invention, are formulated into pharmaceutical compositions or pharmaceutical formulations for parenteral administration, e.g., intravenous; mucosal, e.g., intranasal; enteral, e.g., oral; topical, e.g., transdermal; ocular, e.g., via conical scarification or other mode of administration. The pharmaceutical composition contains a compound according to embodiments of the present invention in combination with one or more pharmaceutically acceptable ingredients. The carrier may be in the form of a solid, semi-solid or liquid diluent, cream or a capsule. These pharmaceutical preparations are a further object of the invention. Usually the amount of active compounds is between 0.1-95% by weight of the preparation, are for example, between 0.2-20% by weight in preparations for parenteral use and are, for example, between 1 and 50% by weight in preparations for oral administration.

The terms "parenteral administration," "administered parenterally," and like terms, as used herein, refer to modes of administration other than enteral and topical administration, usually by injection, and includes, without limitation, intravenous, intramuscular, intraarterial, intrathecal, intraventricular, intracapsular, intraorbital, intracardiac, intradermal, intraperitoneal, transtracheal, subcutaneous, subcuticular, intraarticular, sub capsular, subarachnoid, intraspinal, intracerebro spinal, and intrasternal injection and infusion. The phrases "systemic administration," "administered systemically," "peripheral administration," "administered peripherally," and like terms, as used herein, refer to the administration of a compound, drug or other material other than directly into the central nervous system, such that it enters the subject's system and, thus, is subject to metabolism and other like processes, for example, subcutaneous administration.

Cancers in FA Patients

The aberrant mechanisms in Fanconi anemia (FA) overlap with tumorigenesis, thereby predisposing FA patients to cancer. For any cancer in an FA patient that requires chemotherapy and/or radiation, inhibition of DNA2 stabilizes the cells of the FA patient. Some of the more common cancers seen in FA patients include acute myeloid leukemia (AML), acute lymphoid leukemia (ALL), T-cell ALL, head and neck squamous cell carcinoma (HNSCC), oesophageal cancer, gynecological cancers, liver cancers, medulloblastoma, neuroblastoma, Wilms tumor, breast cancer, ovarian cancer, prostate cancer, hemangioendothelioma, non-Hodgkin's lymphoma, skin cancers, colon cancer, and basal and squamous cell carcinoma of the skin (Kottemann and Smogorzewska, 2013, supra).

For the treatment of cancer in an FA cancer patient, inhibition of DNA2 according to embodiments of the present invention, may be prior to, or in combination with administration of a chemotherapeutic agent and/or radiation therapy. Examples of chemotherapeutic agents are known in the art, non-limiting examples of which include Actinomycin, All-trans retinoic acid, Azacitidine, Azathioprine, Bleomycin, Bortezomib, Carboplatin, Capecitabine, Cisplatin, Chlorambucil, Cyclophosphamide, Cytarabine, Daunorubicin, Docetaxel, Doxifluridine, Doxorubicin, Epirubicin, Epothilone, Etoposide, Fluorouracil, Fludarabine, Gemcitabine, Hydroxyurea, Idarubicin, Imatinib, Irinotecan, Mechlorethamine, Mercaptopurine, Methotrexate, Mitoxantrone, Oxaliplatin, Paclitaxel, Pemetrexed, Teniposide, Tioguanine, Topotecan, Valrubicin, Vinblastine, Vincristine, Vindesine, Vinorelbine, and a combinations thereof.

The following Examples are presented for illustrative purposes only, and do not limit the scope or content of the present application.

Examples

Reference is made to Karanja et al., 2014, *Cell Cycle*, 13:1-11, the entire contents of which are incorporated herein by reference.

Example 1

Figure 2A:
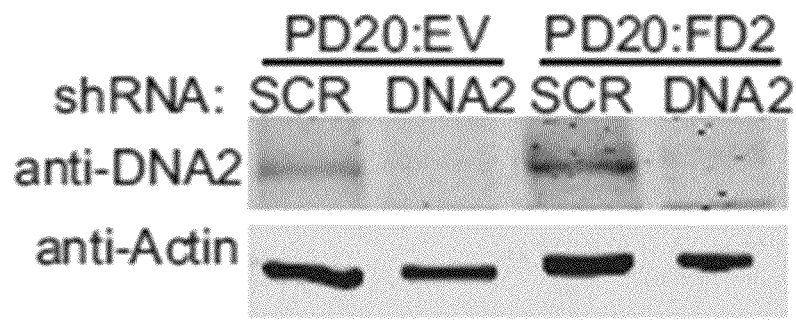
FIG. 2A is an image of a Western blot of DNA2 (with actin control) in human Fanconi anemia PD20 FANCD2$^{-/-}$ cells (PD20:EV), or PD20 FANCD2$^{-/-}$ cells complemented with wild type FANCD2 (PD20:FD2) using shorthairpin RNA that is scrambled (shSCR) or shRNA targeted to DNA2 at exon 22 (shDNA2), showing that DNA2 is depleted by shDNA2.
Figure 2B:
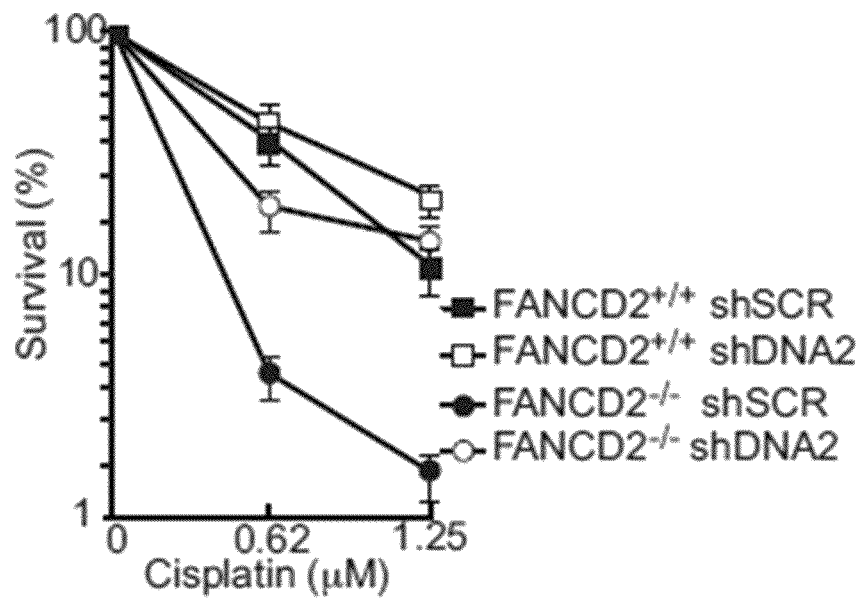
FIG. 2B is a graph comparing the percent clonogenic survival of the FANCD2$^{-/-}$ (PD20:EV) cells or PD20:FD2 cells (labeled as FANCD2$^{+/+}$) carrying shSCR or shRNA in the presence of the indicated doses of cisplatin.

Cisplatin and Formaldehyde Sensitivity of FANCD2-Deficient Cells are Rescued after DNA2 Depletion The genetic interaction between FANCD2 and DNA2 was examined in the repair of cisplatin- or formaldehyde-induced damage. Using PD20 FANCD2$^{-/-}$ cells complemented with wild-type FANCD2 or an empty vector, DNA2 was depleted using shRNA techniques (FIG. 2A). As shown, DNA2 was reduced to levels undetectable by western blotting. The cell lines were exposed to cisplatin, and a clonogenic assay was performed (FIG. 2B). The FANCD2$^{-/-}$ cells were very sensitive to cisplatin whereas the FANCD2$^{-/-}$ cells complemented with FANCD2 were resistant. However, in shDNA2 and FANCD2$^{-/-}$ doubly-deficient cells, instead of increased ICL sensitivity, significant ($p<0.05$) resistance to cisplatin damage compared to FANCD2$^{-/-}$ deficient cells alone was observed (FIG. 2B). This rescue is stronger than previously reported, consistent with lower residual DNA2 levels detected by western blotting in the knockdowns (Karanja et al., 2012, *Cell Cycle*, 11:3983-3996, the entire contents of which are herein incorporated by reference.)

Figure 3A:
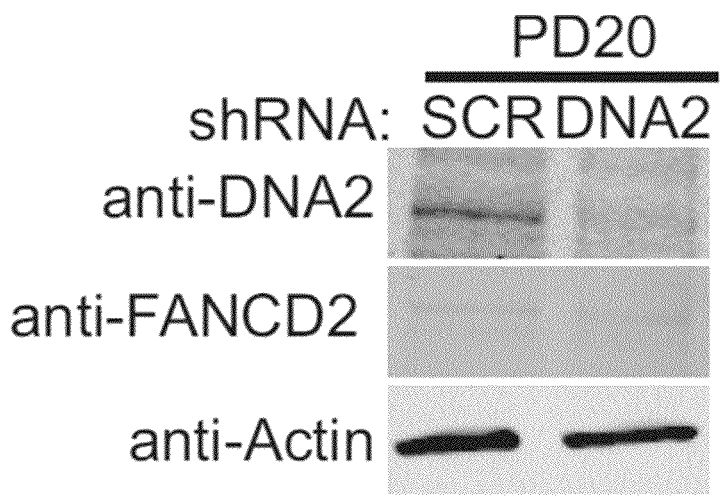
FIG. 3A is an image of a Western blot of DNA2 and FANCD2 (with actin control) in FANCD2$^{-/-}$ (PD20:EV) cells confirming the absence of FANCD2 and the depletion of DNA2 by shDNA2.
Figure 3B:
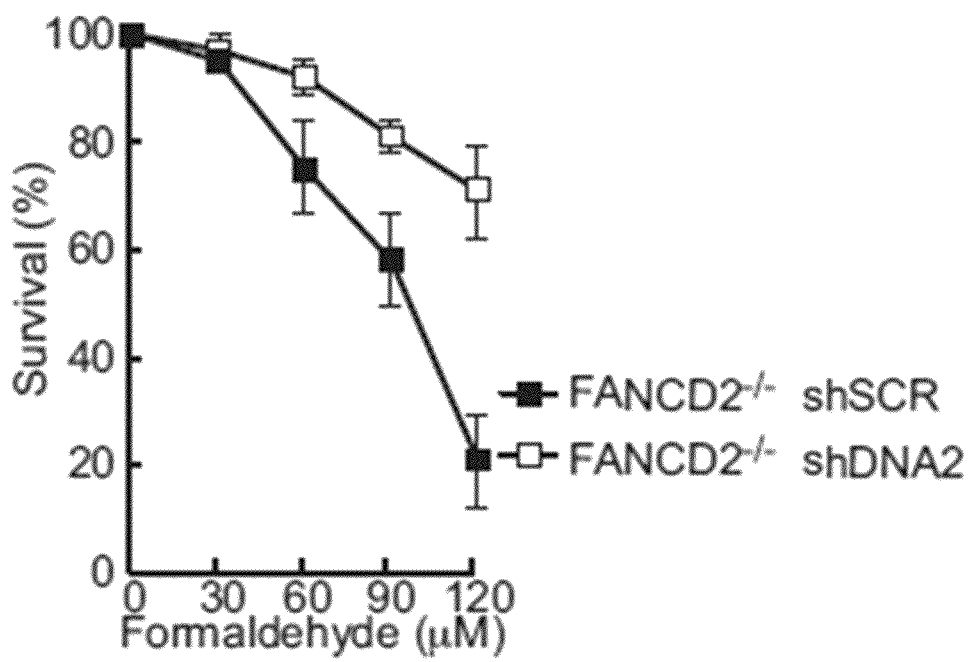
FIG. 3B is a graph comparing the percent clonogenic survival of the FANCD2$^{-/-}$ (PD20:EV) cells shown in FIG. 3A carrying shSCR or shRNA in the presence of the indicated doses of formaldehyde.

In addition to DNA:DNA crosslinks generated by clastogenic agents such as cisplatin, the FA/BRCA pathway is also implicated in the repair of DNA:protein crosslinks (DPCs), such as those produced by either endogenous or exogenous formaldehyde (HCHO), as disclosed in Rosado et al., 2011, *Nature Struct. & Molec. Bio.*, 18:1432-1434, the entire contents of which are herein incorporated by reference. FANCD1/BRCA2- and FANCD2-deficient cells are hypersensitive to endogenous levels of formaldehyde, and in chicken DT40 cells, mutations in the ADH5 gene, encoding a major formaldehyde-detoxifying enzyme, are synthetically lethal with FANCD2$^{-/-}$, implying that the FA pathway is vital for DPC repair (Rosado et al., 2011, supra, and Ridpath et al. 2007, *Cancer Research*, 67:11117-11122, the entire contents of both of which are herein incorporated by reference. Whether DNA2 depletion could also suppress formaldehyde sensitivity in PD20 FANCD2$^{-/-}$ was also tested. For this test, cells were exposed to formaldehyde, grown for 48 hours (h), and the surviving fraction was determined. As with cisplatin, the DNA2 knockdown:FANCD2$^{-/-}$ cells were significantly less sensitive to formaldehyde than the FANCD2$^{-/-}$ deficient cells (FIGS. 3A, 3B). Thus, depletion of DNA2 suppresses the sensitivity of FANCD2$^{-/-}$ cells to formaldehyde, as well as to cisplatin.

Example 2

DNA2-Depleted Cells are Hypersensitive to Formaldehyde

Figure 4A:
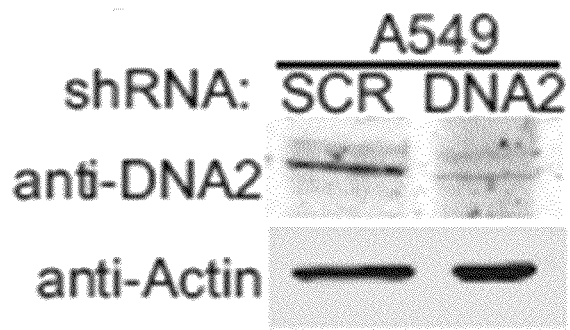
FIG. 4A is an image of a Western blot of DNA2 (with actin control) in A549 lung carcinoma cells depleted carrying shDNA2 or shSCR.
Figure 4B:
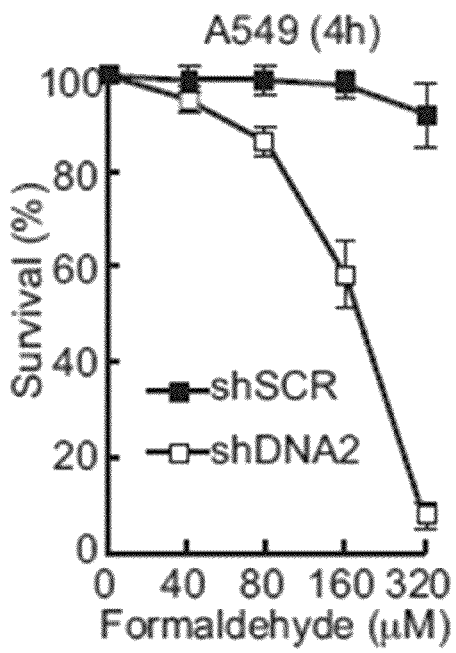
FIG. 4B is a graph comparing the percent clonogenic survival of A549 cells after 4 hours carrying shSCR or shRNA, in the presence of the indicated doses of formaldehyde.
Figure 4C:
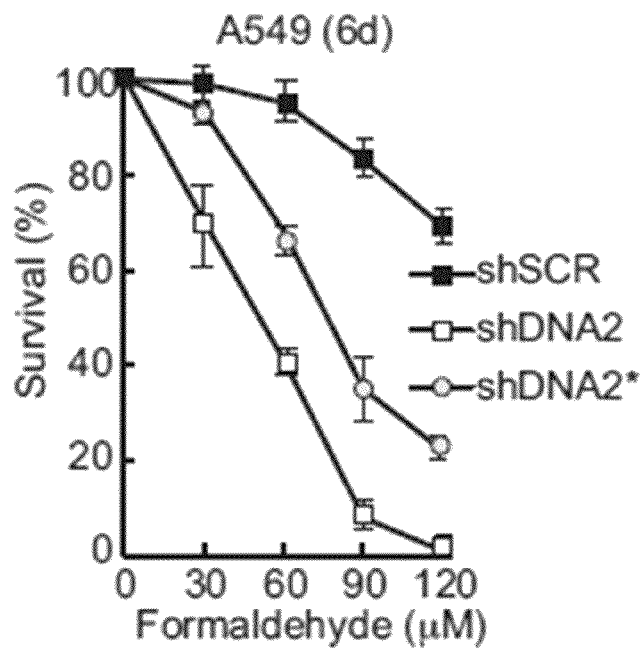
FIG. 4C is a graph comparing the percent clonogenic survival of A549 cells after 6 days carrying shSCR, shDNA2 or shDNA2* (targeting the 3' UTR of exon 22), in the presence of the indicated doses of formaldehyde.
Figure 5A:
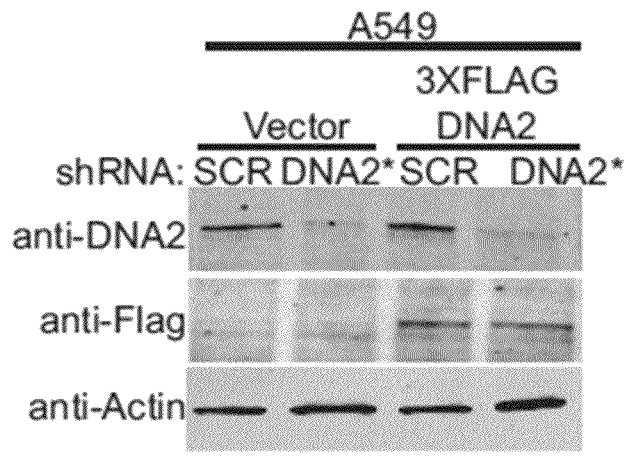
FIG. 5A is an image of a Western blot of DNA2 (with actin control) in A549 cells carrying shSCR or shDNA2* and A549 cells complemented with RNAi-resistant DNA2 (3×-FLAG-DNA2) carrying shSCR or shDNA2*.
Figure 5B:
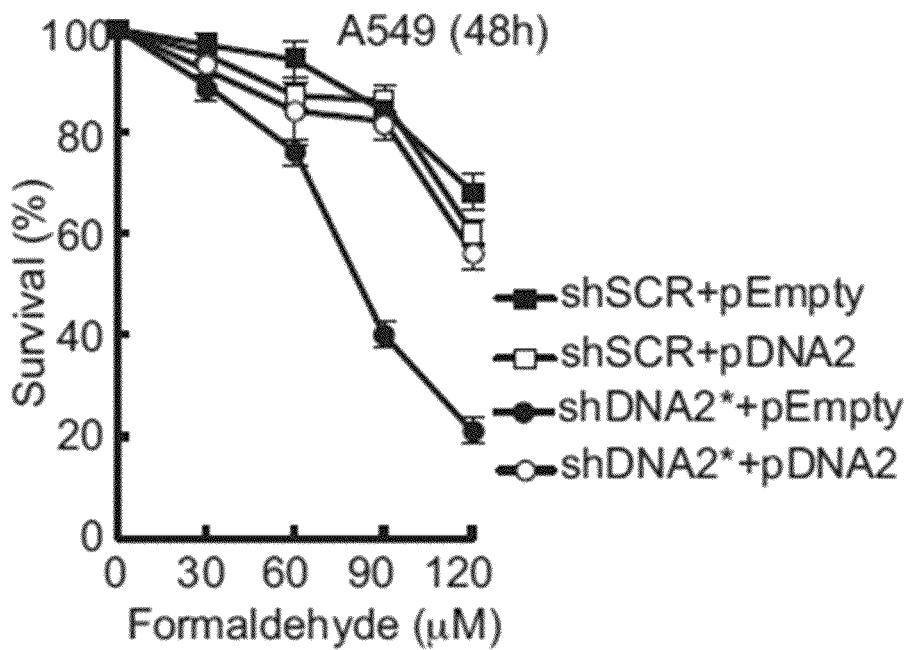
FIG. 5B is a graph comparing the percent clonogenic survival of A549 cells after 48 hours carrying shSCR or shDNA2* with empty vector (pEmpty) and A549 cells complemented with 3×-FLAG-DNA2 (pDNA2) or pEmpty in the presence of the indicated doses of formaldehyde.
Figure 6A:
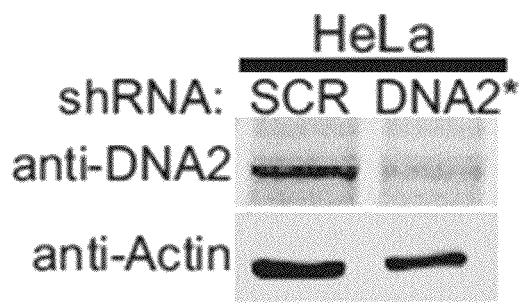
FIG. 6A is a Western blot of DNA2 (with actin control) in HeLa cells carrying shSCR or shDNA2*.
Figure 6B:
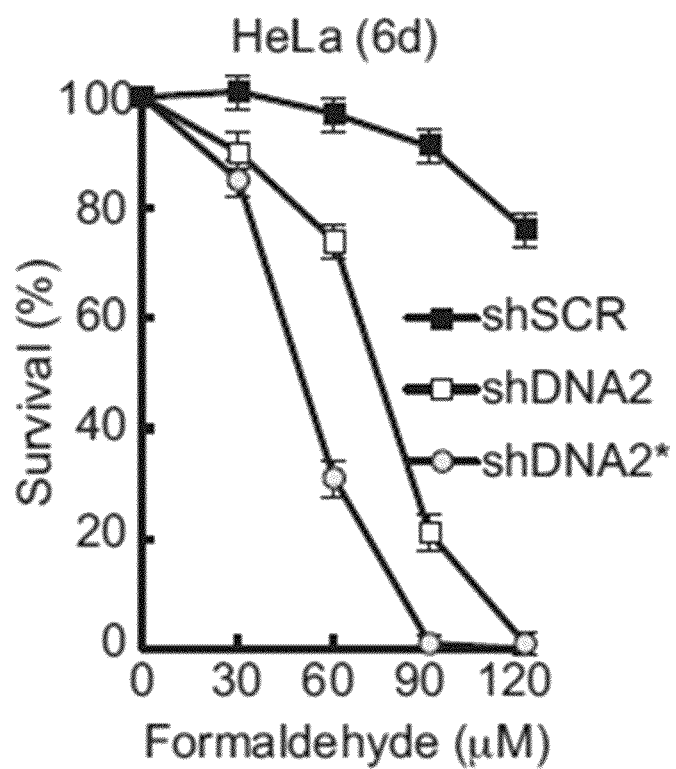
FIG. 6B is a graph comparing the percent clonogenic survival of human cervical cancer cells (HeLa) after 6 days carrying shSCR, shDNA2, or shDNA2* in the presence of the indicated doses of formaldehyde.

To further implicate DNA2 in the FA/B RCA network, it was determined if DNA2 might be required for the repair of DPC lesions, by testing whether DNA2 deficiency results in elevated formaldehyde sensitivity. For this, DNA2 was depleted in FANCD2-proficient cells prior to exposure to formaldehyde and cell survival was measured after a short exposure to high doses of formaldehyde (FIGS. 4A, 4B, and 4C). As shown, DNA2-depleted lung cancer cells were hypersensitive to formaldehyde (FIG. 4B). Similar studies were performed for chronic exposure to low doses of formaldehyde (FIG. 4C). Two independent shDNA2 constructs, shDNA2 and shDNA2*, were included which target exon 22 and the 3'UTR of DNA2, respectively, to ascertain whether the results were DNA2-specific. The cells were exposed to low doses of formaldehyde for 6 days and assayed for survival, and the doses of formaldehyde were within the range of physiological concentration in human plasma as disclosed in Heck et al., 2004, $RTP$, 40:92-106, the entire contents of which are herein incorporated by reference. A significant increase in cellular sensitivity to formaldehyde after DNA2 depletion was observed (FIG. 4C). To further confirm that the formaldehyde sensitivity was due to the DNA2 depletion, and not off-target effects, complementation experiments were performed where shDNA2* was co-introduced into cells with expressed recombinant, RNAi-resistant DNA2. The A549 cells expressing an empty vector were hypersensitive to formaldehyde, however, the cells expressing RNAi resistant-DNA2 were able to repair the DPCs (FIGS. 5A, 5B). DNA2-depleted HeLa cells were as sensitive to formaldehyde as the lung cancer A549 cells (FIGS. 6A, 6B). Accordingly, as shown in FIGS. 2A-6B, depletion of DNA2 leads to sensitivity to ICLs and DPCs in human cell lines.

Figure 7A:
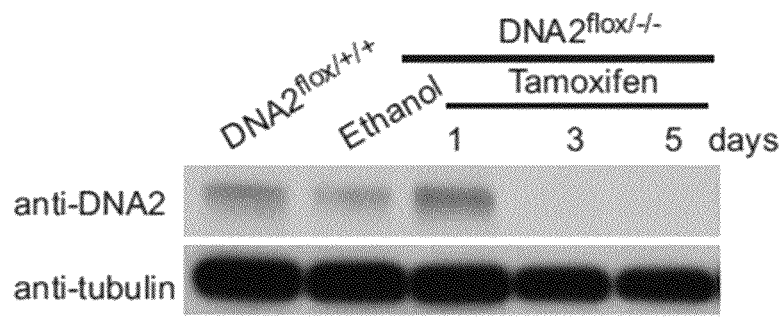
FIG. 7A is a Western blot of DNA2 (with tubulin control) in human colorectal cancer cells (HCT116). DNA2$^{flox/-/-}$ represents HCT116 cells in which 2 of the 3 alleles of DNA2 are disrupted and the 3rd allele of DNA2 is replaced with a conditional exon flanked by loxP sites (DNA2$^{flox/-/-}$), which upon addition of tamoxifen to the cell culture results in excision of the last DNA2 allele, rendering a DNA2 null cell. DNA2$^{flox/+/+}$ represents HCT116 cells in which 1 of the 3 alleles of DNA2 is replaced with a conditional exon flanked by loxP sites (DNA2$^{flox/-/-}$), which upon addition of tamoxifen to the cell culture results in excision of 1 allele. Tamoxifen or ethanol was added to DNA2$^{flox/-/-}$ cells and grown for 1, 3, or 5 days as indicated, and ethanol was added to DNA2$^{flox/+/+}$ cells.
Figure 7B:
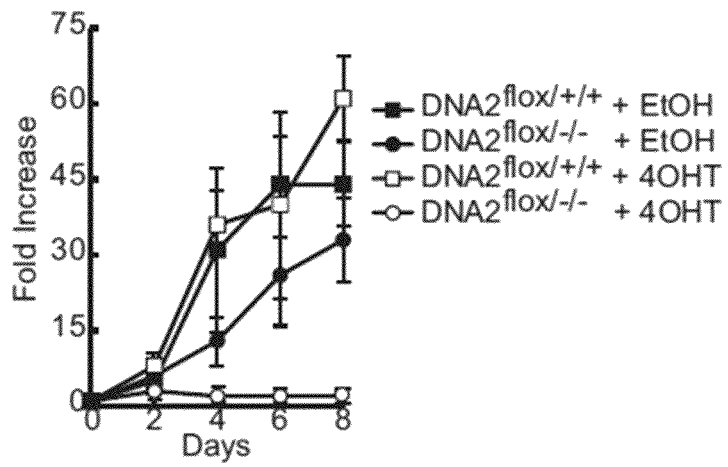
FIG. 7B is a graph comparing the fold increase in cell proliferation after complete DNA2 knockout in DNA2$^{flox/-/-}$ cells and in DNA2$^{flox/+/+}$ cells in the presence of tamoxifen (4OHT) or ethanol (EtOH) at 0, 2, 4, 6, and 8 days as indicated.

FANCD2 competent cells lacking DNA2 are resistant to cisplatin in the presence of EXO1. However, such cells were sensitive to formaldehyde, even in the presence of EXO1 (FIGS. 4A-6C). Interestingly, depletion of FANCD2 reduces the need for DNA2 in formaldehyde-induced damage repair (FIGS. 7A, 7B).

Figure 7C:
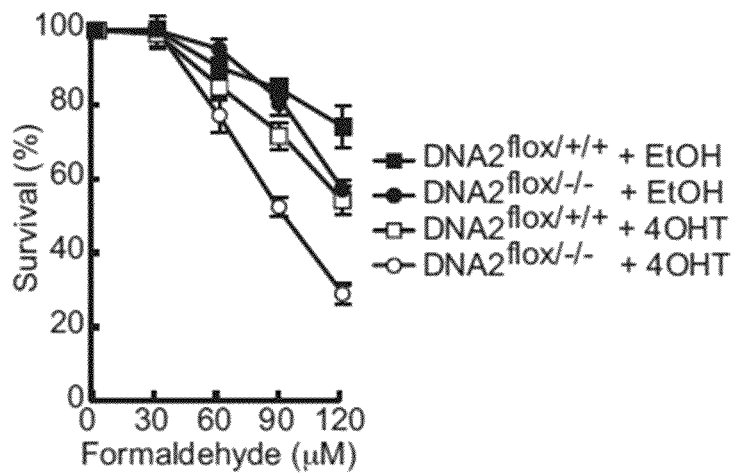
FIG. 7C is a graph comparing the percent clonogenic survival of DNA2$^{flox/-/-}$ cells and DNA2$^{flox/+/+}$ cells in the presence of tamoxifen (4OHT) or ethanol (EtOH) and the indicated doses of formaldehyde.

Because shRNA in cells cease to express the targeting construct after approximately 5 days in culture, and no more than 70-80% depletion of DNA2 was observed. To examine the response of cells to the complete absence of DNA2, a conditional knockout line where exon 2 of the DNA2 gene is deleted was generated. The colorectal carcinoma HCT116 cell line that is otherwise diploid carries three copies of DNA2 due to a small duplication on one copy of chromosome 10 (Fattah et al., 2008, $PNAS$, 105:8703-8708, the entire contents of which are herein incorporated by reference). Two chromosomal copies were disrupted using rAAV-mediated gene targeting technology (Fattah et al., 2008, supra, and Russell et al., 1998, $Nature\ Genetics$, 18:325-330, the entire contents of both of which are herein incorporated by reference), and exon 2 of the third allele was replaced with a conditional exon where the exon was flanked by loxP sites (DNA2$^{flox/-/-}$). These cells were additionally engineered to express a tamoxifen (4-OHT)-inducible Cre recombinase. Thus, the cell line is viable and may be propagated, but the addition of tamoxifen to the culture media leads to excision of the endogenous DNA2 and the generation of a true DNA2-null cell (FIG. 7A). DNA2-proficient cells (treated with ethanol, EtOH) actively replicated while DNA2-deficient cells did not proliferate, but remained viable for the course of 8 days (FIGS. 7A, 7B). The sensitivity of these tamoxifen (4OHT)-treated cells to formaldehyde was examined (FIG. 7C). The cells were treated with tamoxifen for 48 hours (h), and then exposed to formaldehyde for a further 48 h before fixation, staining and quantitation using Licor Odyssey scanner. DNA2-deficient cells were significantly more sensitive to formaldehyde than the controls (FIG. 7C). At the higher exposure concentration, heterozygotes were also more sensitive than cells carrying three wild-type copies of DNA2.

Example 3

Over-Resection Inhibits Crosslink-Triggered Repair

Figure 8A:
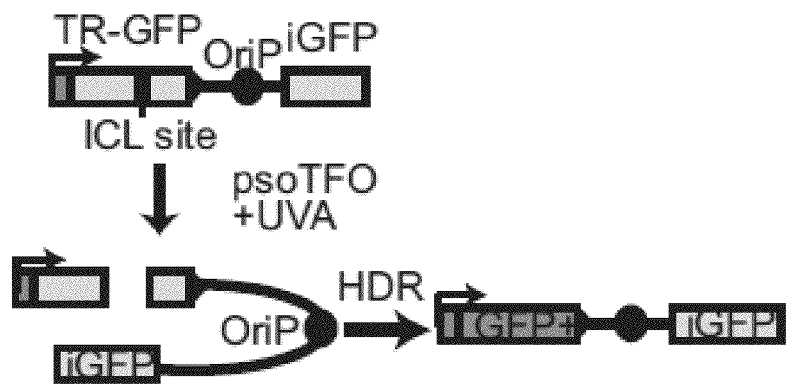
FIG. 8A is a schematic of the TR-oriP-GFP reporter construct used to examine repair after ICL (interstrand crosslink) generation in human osteosarcoma (U2OS) cells using a psoralen triplex forming oligonucleotide (pso-TFO).
Figure 8B:
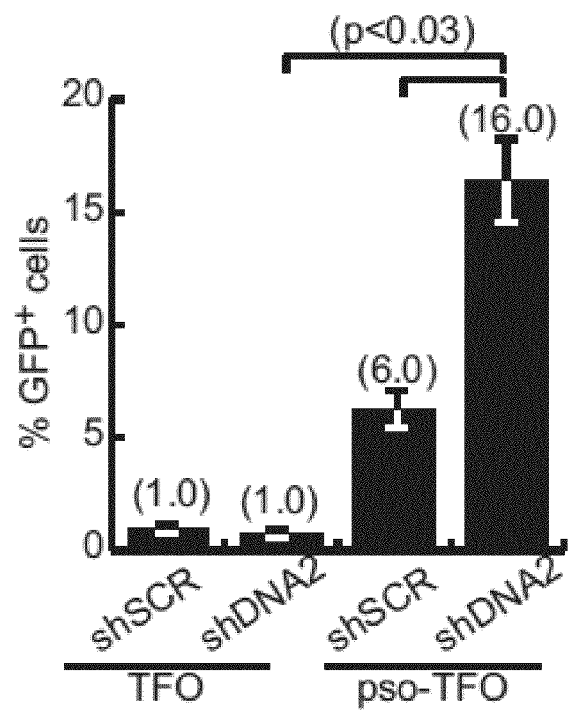
FIG. 8B is a graph comparing the percent GFP+ cells of U2OS cells with TFO (without psoralen) construct or pso-TFO construct carrying shSCR or shDNA2.

The experiments in this section show that DNA2 knockdown reduces unwanted resection at an early step in the FA pathway, thus increasing HDR. To investigate if DNA2 depletion increases ICL- or DPC-induced repair, various repair-specific reporter constructs were tested. ICL repair was monitored using a plasmid-encoded TR-oriP-GFP with a conjugated psolaren moiety (pso-TFO) to deliver the psolaren to a specific site within the GFP gene in the construct (Nakanishi et al., 2011, $Nature\ Struct.\ \&\ Molec.\ Bio.$, 18:500-503, the entire contents of which are herein incorporated by reference.) After exposure to UV, a DNA:DNA crosslink is formed which, when efficiently repaired, leads to GFP expression. The plasmid carrying the reporter also has an Epstein Barr virus (EBV) origin of replication (oriP), and the U2OS cells in which these experiments were performed express the Epstein Barr Nuclear Antigen (EBNA1) replication initiation protein. Thus, repair of the resulting crosslink is coupled to DNA replication. This repair is dependent on both early (FANCA) and late (e.g., HDR proteins such as BRCA2, RAD51) acting components of the FA pathway and is a specific measure of ICL-induced repair as disclosed in Nakanishi et al., $Methods\ Mol\ Biol$ 2011, 745:283-291, the entire contents of which are herein incorporated by reference. DNA2 was depleted in cells containing the TR-ori-GFP construct, and unlike cells with BRCA2 depletion, which showed a reduction of GFP cells, a significant ($p<0.03$) increase in GFP cells using shDNA2 depletion (16%) was observed compared to shSCR controls (6%) (FIG. 8A). Accordingly, in wild type (shSCR-treated) cells, DNA2 was responsible for excess resection resulting in reduced repair of this specific construct. After depletion, the cells were better able to repair the ICL damage and yield an increase in GFP$^+$ cells (using EXO1 or residual DNA2).

Figure 9A:
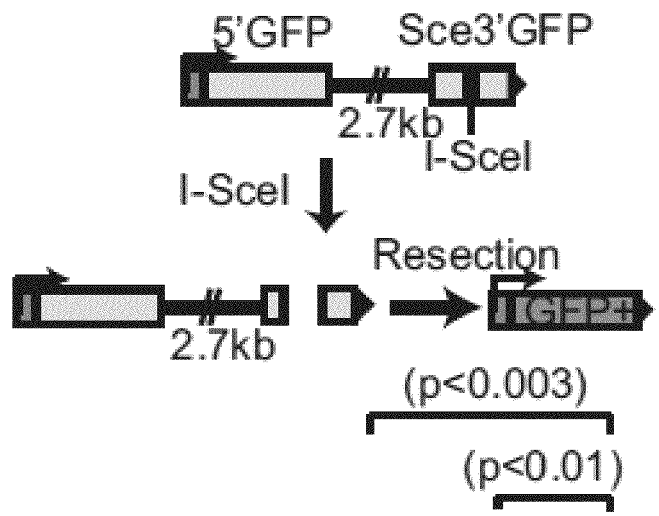
FIG. 9A is a schematic of the strand annealing (SA)-GFP reporter construct used to examine resection after I-SceI-induced double strand breaks (DSB) in U2OS cells.
Figure 9B:
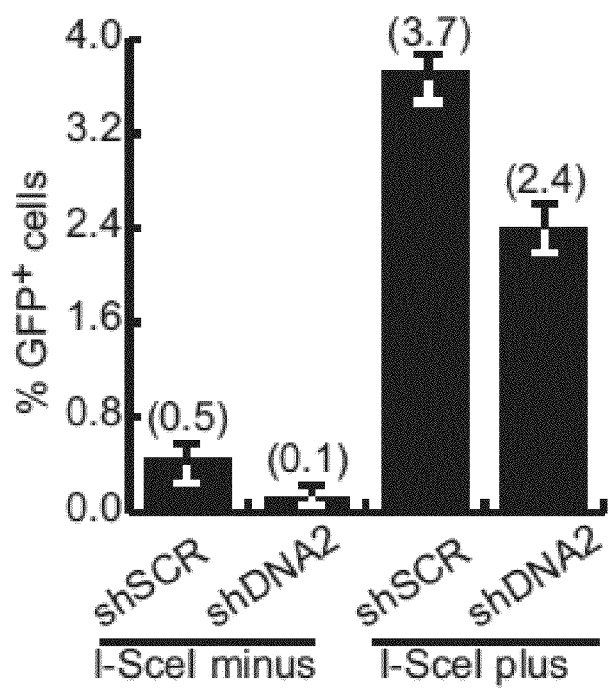
FIG. 9B is a graph comparing the percent GFP+ cells of U2OS cells carrying the SA-GFP reporter carrying shSCR or shDNA2 in the presence or absence of I-SceI.
Figure 10A:
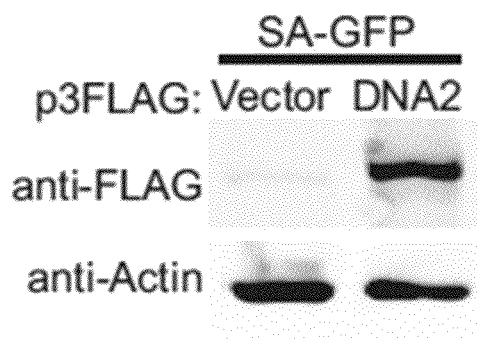
FIG. 10A is a Western blot of FLAG protein (with actin control) of 3×FLAG-DNA2 or vector alone (Vector) in U2OS cells carrying the SA-GFP reporter.
Figure 10B:
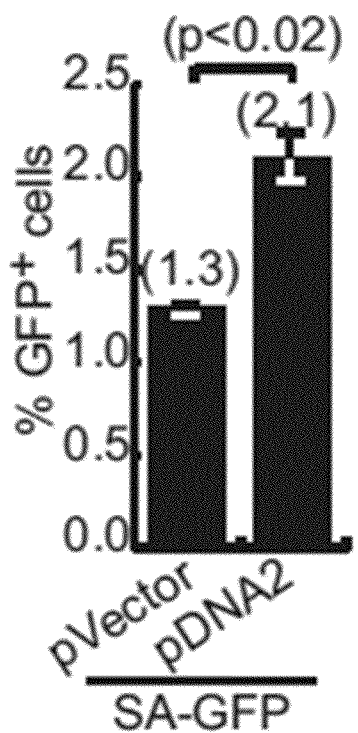
FIG. 10B is a graph comparing the percent GFP+ U2OS cells of the U2OS cells carrying the SA-GFP and either vector alone (pVector) or 3×FLAG-DNA2 (pDNA2).

For further analysis, a different GFP reporter that monitors single-strand annealing (SSA) was tested. SSA involves the repair of DSBs between two repeated sequences (Gunn et al., 2011, $JBC$, 286:42470-42482, the entire contents of which are herein incorporated by reference.) As reported in Gunn et al., SSA requires resection but does not require strand invasion as the two 3'-overhangs simply align and anneal. SSA was measured with the SA-GFP reporter system (Bennardo et al., 2008, $PLoS\ genetics$ 4:e1000110, the entire contents of which are herein incorporated by reference.) GFP$^+$ cells only arise after extensive resection of a 2.7 kb intervening region between two incomplete, but overlapping GFP gene segments. After induction of a DSB by I-SceI, and resection, the two segments align and anneal generating GFP$^+$ cells (FIGS. 9A, 9B). As shown, this reporter decreases production of GFP$^+$ cells in the absence of DNA2. Indeed, a significant reduction ($p<0.01$) in GFP cells in shDNA2-treated cells compared to shSCR controls was observed (FIGS. 9A, 9B). As shown in FIG. 10A, using the same SA-GFP reporter, recombinant DNA2 was overexpressed and repair was measured after I-SceI expression. As shown in FIG. 10B, increasing the cellular pool of DNA2 improved the efficiency of resection. As shown, a robust expression of DNA2 (FIG. 10A) that resulted in a significant increase ($p<0.02$) in GFP$^+$ cells (FIG. 10B). Thus, DNA2 catalyzes extensive resection in these reporter assays.

Figure 11A:
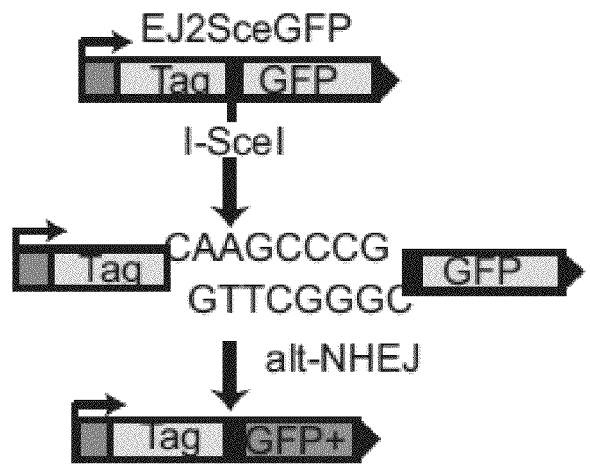
FIG. 11A is a schematic of an end joining 2 (EJ2)SceG FP reporter construct that measures alternative non-homologous end joining (alt-NHEJ) to examine resection of microhomology DNA in U2OS cells after I-SceI expression.
Figure 11B:
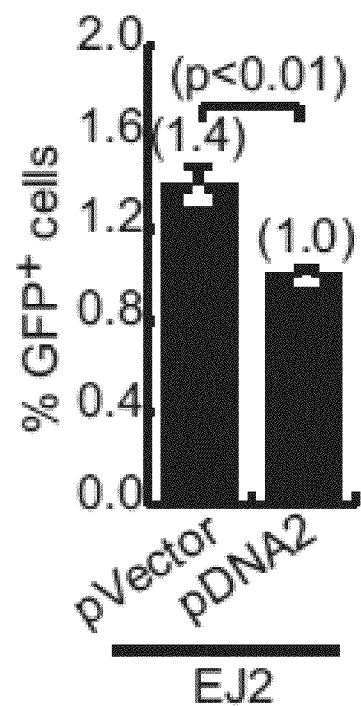
FIG. 11B is a graph comparing the percent GFP+ U2OS cells of the U2OS cells carrying EJ2SceGFP and either vector alone (pVector) or 3×FLAG-DNA2 (pDNA2).
Figure 12A:
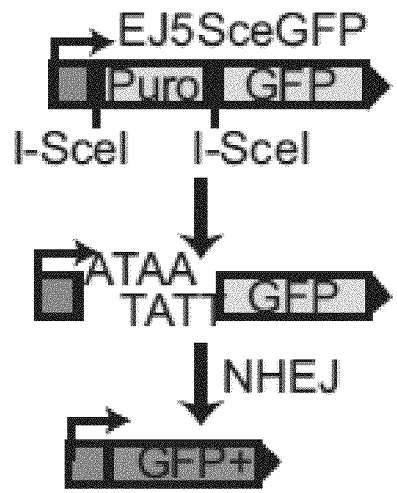
FIG. 12A is a schematic of an end joining 5 (EJ5)SceGFP reporter construct that measures resection of DNA after I-SceI expression.
Figure 12B:
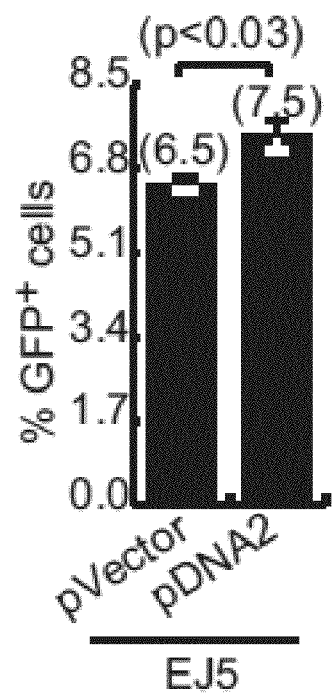
FIG. 12B is a graph comparing the percent GFP+ U2OS cells of the U2OS cells carrying EJ5SceGFP and either vector alone (pVector) or 3×FLAG-DNA2 (pDNA2).

FANCD2-deficient cells have increased chromosomal aberrations attributed to NHEJ (Pace et al., 2010, *Science*, 329:219-223 and Adamo et al., 2010, *Molecular Cell*, 39:25-35, the entire contents of both of which are herein incorporated by reference). FIG. 11A shows a GFP expression reporter construct for testing the ability of DNA2 to resect DNA at DSB ends that are designed to be repaired by NHEJ (Bernnardo et al., 2008, supra). Specifically, the EJ2SceGFP construct as depicted, measures alternative NHEJ (alt-NHEJ), a process that utilizes microhomology immediately adjacent to DSB ends for repair. Resection by DNA2 of the microhomology regions after DSB induction would be expected to decrease the efficiency of alt-NHEJ. To test the effect of DNA2, the DNA2 protein was overexpressed, and $GFP^+$ cells were enumerated by flow cytometry. As shown in FIG. 11B, a significant ($p<0.01$) reduction in $GFP^+$ cells among cells overexpressing DNA2 in comparison to controls. Next, the EJ5SceGFP construct as depicted in FIG. 12A, was used to measure total NHEJ which takes into account DSBs repaired by both alt-NHEJ and canonical NHEJ. Using this reporter, trimming at the sites of al-SceI-induced DSB is required to efficiently generate substrates for canonical NHEJ. Impairment of alt-NHEJ does not affect the readout because removal of microhomology regions produces a substrate for canonical NHEJ. As shown in FIG. 12B, a small, but significant ($p<0.03$) increase in $GFP^+$ cells was observed after expression of DNA2 compared to vector control. Since overexpression of DNA2 reduced alt-NHEJ (presumably because of over-resection), using a construct that favors resection for repair increased $GFP^+$ cells. Thus, DNA2 upregulation increases resection at I-SceI-induced breaks, regardless of the configuration of the breaks.

Example 4

FANCD2 Foci Formation is not Affected by DNA2 Depletion

Figure 13A:
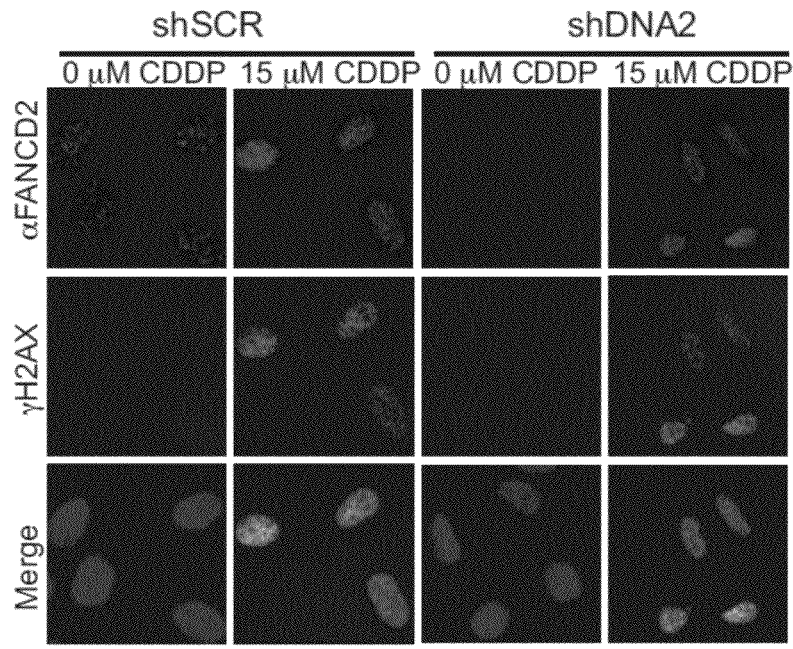
FIG. 13A includes immunofluorescence images of U2OS cells carrying shSCR or shDNA2 as indicated, with 0 or 15 µM cisplatin, stained with anti-FANCD2 or γH2Ax antibodies.
Figure 13B:
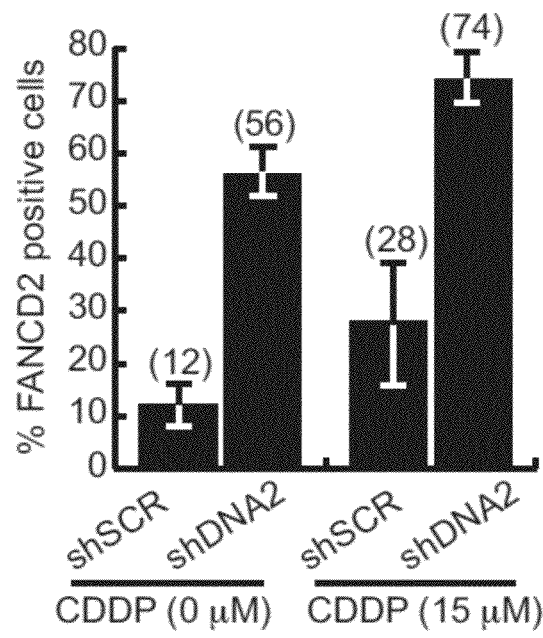
FIG. 13B is a graph comparing the percent FANCD2 foci positive cells that are also positive for γH2Ax of the U2OS cells shown in FIG. 13A, according to embodiments of the present invention.
Figure 14A:
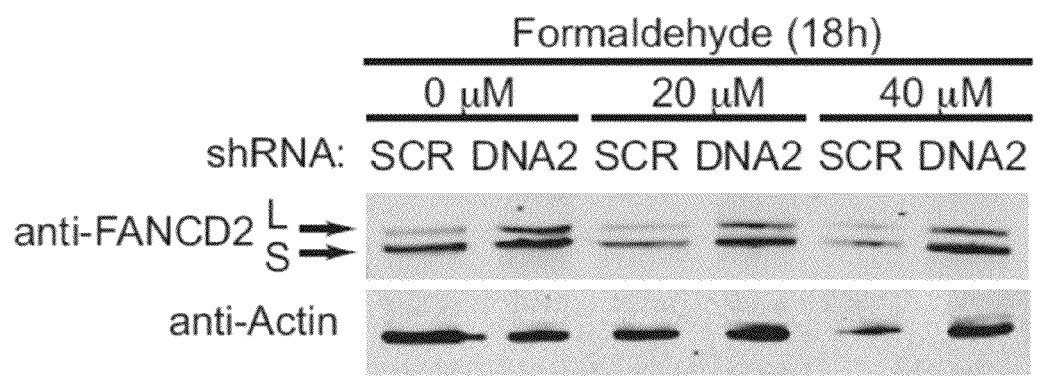
FIG. 14A is a Western blot of FANCD2 (L=ubiquitylated and S=no ubiquitylation) (with actin control) in A549 cells carrying shSCR or shDNA2, in the presence of the indicated doses of formaldehyde for 18 hours, according to embodiments of the present invention.
Figure 14B:
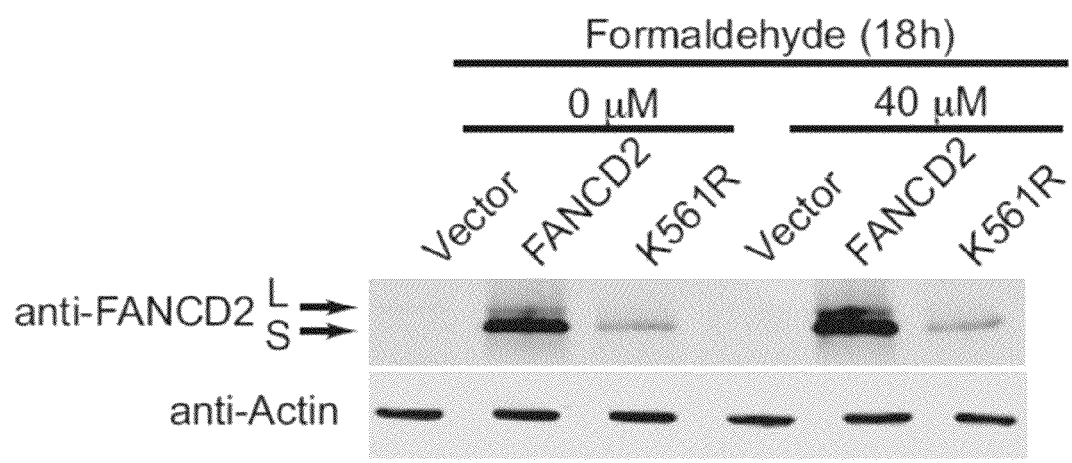
FIG. 14B is a Western blot of FANCD2 (L=ubiquitylated and S=no ubiquitylation) (with actin control) in PD20 FANCD2−/− complemented with empty vector (Vector), wild type FANCD2 vector or FANCD2-K561R vector, according to embodiments of the present invention.

FANCD2 localizes to chromatin at sites of ICL damage where it interacts with BRCA2 and forms immuno-detectable foci. CtIP or Mre11 appear to be involved in an early step in ICL repair, because CtIP or Mre11 depletion prevents FANCD2 recruitment to sites of damage and ubiquitylation of FANCD2 in the presence of ICL damage (Rogues et al., 2009, *EMBO J*, 28:2400-2413 and Ridpath et al., 2007, supra, the entire contents of both of which are herein incorporated by reference). Since CtIP and Mre11 are implicated in resection just upstream of DNA2, it was of interest to test whether DNA2 was also required at an early step for FANCD2 activation. Previously, we showed that the depletion of endogenous DNA2 did not affect FANCD2 ubiquitination after cisplatin treatment (Karanja et al., 2012, supra). FIGS. 13A, 13B, 14A, and 14B show the results of how knockdown of DNA2 knockdown affects FANCD2 foci formation after treatment with ICL-generating cisplatin. As shown in FIGS. 13A, 13B, DNA2-depleted cells were able to accumulate FANCD2 foci after cisplatin treatment. As shown in FIGS. 14A, 14B, DNA2 was similarly dispensable for FANCD2 ubiquitylation after treatment with formaldehyde. The control in these experiments was a FANCD2 K561R that cannot be ubiquitylated (FIG. 14B). FIGS. 13A-13B also show that FANCD2 foci accumulated in DNA2-depleted cells without cisplatin exposure. This accumulation is also seen in cells lacking the DNA2 partner, BLM helicase, as disclosed in Chan et al., 2009, *Nat. Cell Biol.*, 11:753-760, the entire contents of which are herein incorporated by reference. These observations support the proposed role of DNA2 in the HDR step.

Example 5

Cell Culture and Transfections

A549, U2OS, U2OS-DR-GFP[66] U2OS-SA-GFP, EJ2 and EJ5 (Gunn et al., 2011, supra) cells were gifts from Dr. P. Dervan, Dr. W. Dunphy, California Institute of Technology, Dr. M. Jasin, Memorial Sloan-Kettering Cancer Center and Dr. J. Stark, City of Hope, respectively. PD20 $FANCD2^{-/-}$ lines were obtained from the Fanconi Anemia Research Fund. Cells were maintained in Dulbecco's modified Eagle's medium (DMEM) containing 10% heat-inactivated fetal bovine serum (FBS) and 1% penicillin/streptomycin at 37° C. in 5% $CO_2$.

Example 6

Virus Production and Infection

Virus was produced in HEK293T cells as described (Duxin et al., 2009, *Mol. Cell Biol.*, 29:4274-4282, Duxin et al., 2012, *JBC*, 287:21980-21991, and Budd & Campbell, 2009, *PLoS ONE*. 4:e4267, the entire contents of all of which are herein incorporated by reference. Briefly, cells were transfected with pLKO.1.shSCR, pLKO.1.shDna2, pLKO.1.shDna2, or pLKO.1.shDna2* and pCMVAR8.2 and pCMV-VSV-G using BioT (Bioland Scientific) (Duxin et al., 2009, supra and Duxin et al., 2012, supra). Virus was recovered 48 h post-transfection and infections were carried out in cells overnight in the presence of 10 µg/ml of protamine sulfate. Transduced cells were selected with 2 µg/ml of puromycin for 48 h. The following sequences were used for the hDNA2 short hairpins, (SEQ ID NO: 1) 5'-CATAGCCAGTAGTATTCGATG-3' for shDna2, (SEQ ID NO: 2) 5'-CCGGCCAGCTTTGAA-GATGGATTAACTCGAGTTAATCCATCT-TCAAAGCTGGTTTTTG-3' for shDna2*.

Example 7

Construction of Human Conditional DNA2 Null Somatic Cell Lines

The conditional $DNA2^{flox/-/-}$ null HCT116 cell line was constructed with the aid of rAAV (recombinant adeno-associated virus) mediated gene-targeting technology (Fattah et al., 2008, supra and Russell et al., 1998, supra). DNA2 is triploid in the HCT116 cell line and all three alleles were sequentially targeted with a rAAV targeting vector designed with 3 loxP sites flanking the exon and a drug resistance marker. Subsequently, the cell line was also modified to express Cre recombinase under a tamoxifen-inducible promoter. As a control, $DNA2^{flox/+/+}$ cells, which were generated after one round of targeting, were used.

Example 8

Knockdown Rescue Experiment

For complementation studies, virus was produced as described above using plasmids with pLKO.1.shDna2*. After transduction and selection, cells were transfected with pCMV7.1-3×FLAG-DNA2 wildtype, pCMV7.1-3×FLAG-DNA2-nuclease dead or pCMV7.1-3×FLAG-empty vector (Lin et al., 2013, *EMBO J*, 32:1425-1439, the entire contents of which are herein incorporated by reference).

Example 9

Clonogenic and Survival Assays

Briefly for survival assays, 48 h after depletion of DNA2, 50,000 cells were seeded into 24 well plates the day before treatment with drugs. For acute exposure, formaldehyde (0, 40, 80, 160, 320 µM) was added for 4 h in PBS. Cells were washed in PBS and grown for 5 days. For chronic exposure, cells were continuously grown in formaldehyde (0, 30, 60, 90, 120 µM) for 6 days. To determine viability, cells were fixed and stained with crystal violet and scanned with a Licor Odyssey scanner (LiCor Biosciences). The surviving fraction was determined by comparing treated with the non-treated controls. A clonogenic assay was also performed for cisplatin sensitivity by seeding 1000, 2000, or 3000 PD20 cells per well, which were then exposed to cisplatin (0, 0.62, 1.25, 2.5 µM) for 24 h, washed and cultured. Colonies were allowed to form for 14 days prior to fixation, staining with crystal violet and enumeration of visible colonies. Surviving fraction was determined by comparing treated with the non-treated controls.

Example 10

Immunofluoresence Microscopy

U2OS cells were grown on poly-L-lysine-coated coverslips and treated with 15 µM cisplatin for 1 h. Cells were pre-extracted with buffer (10 mM HEPES/KOH pH7.4, 300 mM sucrose, 100 mM NaCl, 3 mM $MgCl_2$, 0.5% Triton x-100, 1 mM PMSF, protease and phosphatase inhibitors) and fixed with 4% formaldehyde for 25 min at room temperature. After fixation, cells were washed and blocked in 10% FBS/PBS before addition of primary antibodies ($\alpha$-FANCD2, $\alpha$-$\gamma$H2Ax) diluted at 1:1000 in 10% FBS in PBS. Cells were incubated overnight at 4° C., washed in 10% FBS/PBS and stained with secondary antibodies anti-rabbit IgG-Alexa Fluor 488 or anti-mouse IgG-Alex Fluor 594 for 1 h at room temperature. DNA was counterstained with 4',6'-diamidino-2-phenylindole (DAPI, 0.3 µM) and cover slips were mounted on slides with Vectashield mounting agent (Vector Laboratories). Images were acquired using Zeiss Axio epifluoresent microscope and processed with AxioVision Rel. 4.8 (Carl Zeiss) and Adobe Photoshop (Adobe) software.

Example 11

Resection Assay Using GFP Constructs

DNA2 was depleted or expressed from pCMV7.1-3× FLAG-DNA2 vector in TR-oriP-GFP, DR-GFP, SA-GFP, EJ2, or EJ5 containing U2OS cells. Cells were transfected with an empty plasmid, a plasmid carrying the I-SceI endonuclease or a plasmid carrying GFP for 48 h. $GFP^+$ cells were determined by flow cytometry.

Example 12

Statistical Analysis

Student's t-tests were performed at $p<0.05$ for samples with $n>2$.

As disclosed throughout and evidenced by, for example, FIGS. 2B and 3B, inhibition of DNA2 in Fanconi anemia cells stabilizes the FA cells. Inhibition of DNA2 in FA cells allows for safe treatment of cancers in FA patients, a decrease in the lethality of FA cells, a decrease in bone marrow failure of FA patients, and a means for decreasing the incidence of cancer for FA patients.

While the present invention has been illustrated and described with reference to certain exemplary embodiments, those of ordinary skill in the art will understand that various modifications and changes may be made to the described embodiments without departing from the spirit and scope of the present invention, as defined in the following claims.

What is claimed is:

1. A method of decreasing lethality of human Fanconi anemia cells or human Fanconi anemia-like cells, comprising inhibiting a human DNA2 gene, a human DNA2 transcript, and/or a human DNA2 protein, the inhibiting comprising:
   using a viral vector to disrupt the DNA2 gene; and/or
   using interfering RNA (RNAi) to inhibit translation of the DNA2 transcript; and/or
   using acetylation and/or phosphorylation to inhibit post-translational modification of the DNA2 protein in the Fanconi anemia cells or the Fanconi anemia-like cells.

2. The method of claim 1, wherein the inhibiting the DNA2 transcript comprises interfering RNA (RNAi) directed against the DNA2 transcript.

3. The method of claim 1, wherein the Fanconi anemia cells or the Fanconi anemia-like cells are in vitro or in vivo.

4. The method of claim 1, wherein the inhibiting comprises:
   using the viral vector to disrupt the DNA2 gene; and/or
   using the interfering RNA (RNAi) to inhibit translation of the DNA2 transcript.

5. The method of claim 1, wherein the disruption of the DNA2 gene comprises deletion of exon 2.

6. The method of claim 1, wherein the RNAi is shorthairpin RNA (shRNA).

7. The method of claim 6, wherein the shRNA is targeted to exon 22 of the DNA2 gene.

* * * * *

SEQUENCE LISTING

```
<160> NUMBER OF SEQ ID NOS: 2

<210> SEQ ID NO 1
<211> LENGTH: 21
<212> TYPE: DNA
<213> ORGANISM: Artificial Sequence
<220> FEATURE:
<223> OTHER INFORMATION: shorthairpin shDNA2

<400> SEQUENCE: 1
catagccagt agtattcgat g                                      21

<210> SEQ ID NO 2
<211> LENGTH: 58
<212> TYPE: DNA
<213> ORGANISM: Artificial Sequence
<220> FEATURE:
<223> OTHER INFORMATION: Shorthairpin shDNA2*

<400> SEQUENCE: 2
ccggccagct tgaagatgg attaactcga gttaatccat cttcaaagct ggttttttg   58
```